US012678086B2

(12) United States Patent
Chiu et al.

(10) Patent No.: US 12,678,086 B2
(45) Date of Patent: Jul. 14, 2026

---

(54) CHANGING VIEWS OF TIME SERIES WAVEFORMS

(71) Applicant: AVICENA, LLC, Pasadena, CA (US)

(72) Inventors: Wei-min Brian Chiu, Pasadena, CA (US); Derek Rinderknecht, San Gabriel, CA (US); Faisal Amlani, Palaiseau (FR)

(73) Assignee: AVICENA, LLC, Pasadena, CA (US)

( * ) Notice: Subject to any disclaimer, the term of this patent is extended or adjusted under 35 U.S.C. 154(b) by 404 days.

(21) Appl. No.: 18/525,757

(22) Filed: Nov. 30, 2023

(65) Prior Publication Data

US 2024/0180472 A1      Jun. 6, 2024

Related U.S. Application Data

(60) Provisional application No. 63/429,667, filed on Dec. 2, 2022.

(51) Int. Cl.
*A61B 5/347*          (2021.01)
*A61B 5/358*          (2021.01)
*A61B 5/366*          (2021.01)

(52) U.S. Cl.
CPC .............. *A61B 5/347* (2021.01); *A61B 5/358* (2021.01); *A61B 5/366* (2021.01)

(58) Field of Classification Search
None
See application file for complete search history.

(56) References Cited

U.S. PATENT DOCUMENTS

| | | | |
|---|---|---|---|
| 2005/0197586 A1* | 9/2005 | Pearlman | ................. A61B 5/35 600/509 |
| 2009/0088655 A1 | 4/2009 | Vajdic et al. | |

(Continued)

OTHER PUBLICATIONS

Patent Cooperation Treaty, International Search Report and Written Opinion issued in PCT/IB2023/062148, Mar. 7, 2024, pp. 1-10.

(Continued)

*Primary Examiner* — Ankit D Tejani
(74) *Attorney, Agent, or Firm* — Pillsbury Winthrop Shaw Pittman, LLP

(57) ABSTRACT

Electrical ventricular depolarization may be represented by its vectorcardiographic QRS loop, which exists in 3D space. By recognizing that the QRS loop is often a closed trajectory on a plane (2D), it is possible to change (e.g., by rotation, projection, etc.) the single-channel QRS into a different view angle along that plane to provide a viewpoint more favorable for morphologic interpretation. Any monophasic or biphasic single-channel QRS (time series) waveform can be decomposed into the form $x(\alpha, t)=\sin(\alpha t) u(t)$, with t spanning $[0, 2\pi]$, where $u(t)$ is an unchanging intrinsic component that is generally upright and monophasic, and where $\sin(\alpha t)$ is a changeable component of the waveform. This way, $x(\alpha, t)$ may be changed by replacing a parameter of the original changeable component $\sin(\alpha t)$ with a second parameter associated with a target view of the waveform, such as the upright monophasic $\sin(0.5t)$. Meanwhile the intrinsic component remains unchanged during this change.

56 Claims, 18 Drawing Sheets

(56) References Cited

U.S. PATENT DOCUMENTS

| | | | |
|---|---|---|---|
| 2011/0004110 A1* | 1/2011 | Shusterman | G16H 50/20 |
| | | | 600/509 |
| 2011/0040200 A1 | 2/2011 | Douglas et al. | |
| 2012/0330170 A1 | 12/2012 | Chiu et al. | |
| 2022/0087614 A1 | 3/2022 | Ko et al. | |
| 2022/0202344 A1 | 6/2022 | Chen et al. | |

OTHER PUBLICATIONS

European Patent Office, Extended European Search Report issued in corresponding EP 23897043.8, Nov. 21, 2025, pp. 1-11.
Lee, T.L., "An Amplitude-Modulation Model for the QRS Complexes of Electrocardiograms", IEEE Transactions on Biomedical Engineering, Sep. 1974, pp. 382-386.

* cited by examiner

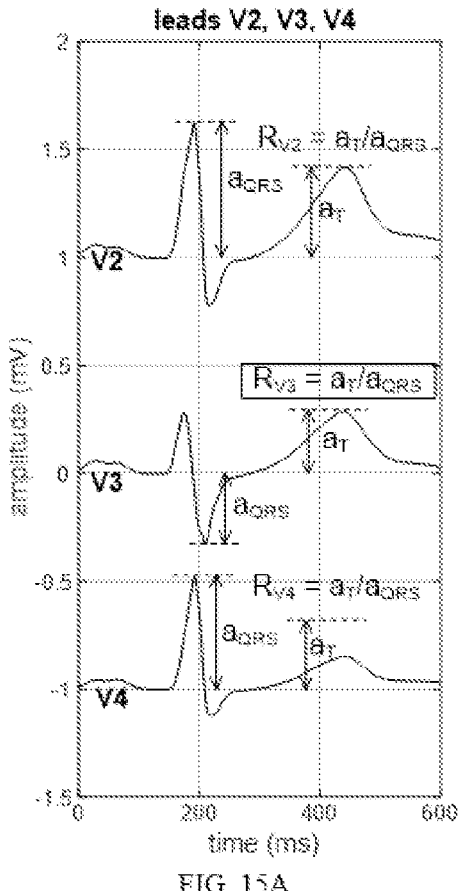
FIG. 15A
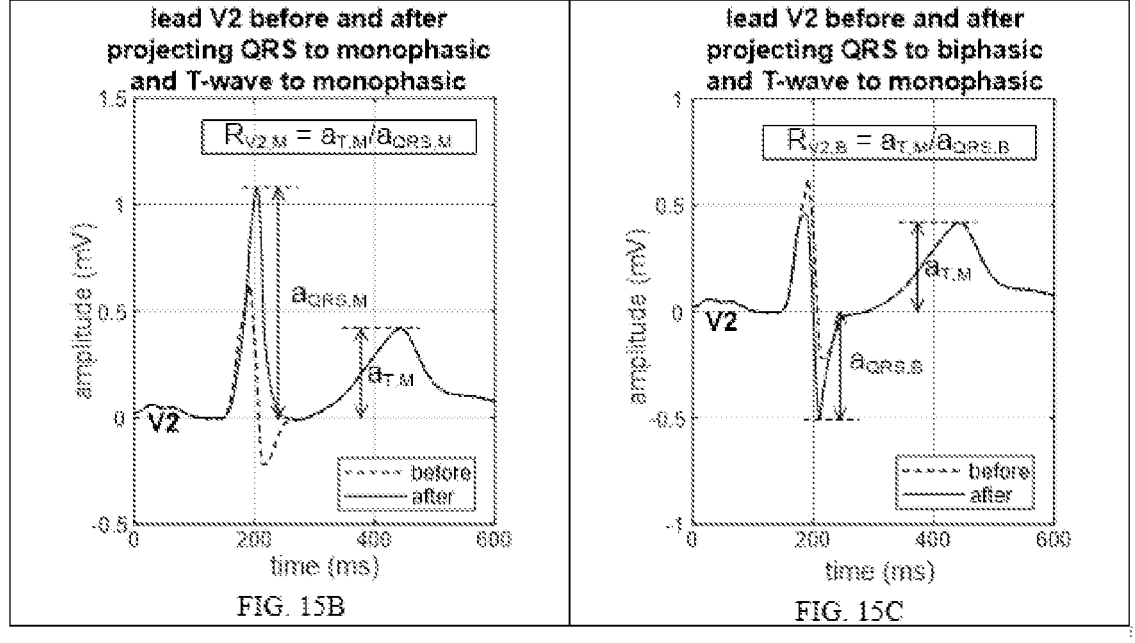
FIG. 15B    FIG. 15C
FIG. 15

CHANGING VIEWS OF TIME SERIES WAVEFORMS

BACKGROUND

1. Field

The present disclosure relates to changing views (e.g., by rotation, projection, and/or other techniques) of time series waveforms.

2. Description of the Related Art

Single-channel electrocardiogram (ECG) devices are widely deployed in patches, watches, exercise equipment, etc. For rhythm interpretation such as that for tachycardia or atrial fibrillation, the single-channel ECG can provide consistent rhythm information. But for morphologic interpretation of a QRS waveform, such as that for intraventricular blocks or ST abnormalities, the single-channel ECG can only provide a shape that is arbitrary, depending on its lead vector relative to the vector of a subject's QRS axis.

SUMMARY

The following is a non-exhaustive listing of some aspects of the present techniques. These and other aspects are described in the following disclosure.

Electrical ventricular depolarization may be represented by its vectorcardiographic QRS loop, which exists in 3D space. By recognizing that the QRS loop is often a closed trajectory on a plane (2D), it is possible to change (e.g., by rotation, projection, etc.) the single-channel QRS into a different view angle along that plane to provide a viewpoint more favorable for morphologic interpretation.

Any monophasic or biphasic single-channel QRS (time series) waveform can be decomposed into the form $x(\alpha, t) = \sin(\alpha t) u(t)$, with $t$ spanning $[0, 2\pi]$, where $u(t)$ is an unchanging intrinsic component that is generally upright and monophasic, and where $\sin(\alpha t)$ is a changeable component of the waveform. This way, $x(\alpha, t)$ may be changed by replacing a parameter (e.g., $\alpha$) of the original changeable component $\sin(\alpha t)$ with a second parameter associated with a target view of the waveform, such as the upright monophasic $\sin(0.5t)$. Meanwhile the intrinsic component remains unchanged.

With this decomposition, for the same QRS loop, the $x(1.0, t)$ projection appears as a "QRS" that is exactly biphasic (RS-pattern). The $x(0.75, t)$ projection appears as a biphasic "QRS" with an R-wave and a small S-wave (Rs-pattern). The $x(0.5, t)$ projection appears as an exactly monophasic "QRS" (R-pattern).

By recognizing that any monophasic or biphasic QRS can be decomposed into an intrinsic component and a changeable component, it is possible to take a single-channel ECG and create a projection along a planar QRS loop that is more favorable for morphologic interpretation.

Some aspects of the present techniques include a method for changing a first view of a time series waveform to a second view. The method comprises separating the first view of the time series waveform into an unchanging intrinsic component and a changeable parameterized component. The method comprises replacing a first parameter of the changeable parameterized component associated with the first view with a second parameter associated with the second view. The method comprises changing the first view to the second view based on the unchanging intrinsic component and the changeable parameterized component with the second parameter.

Some aspects of the present techniques include a non-transitory computer readable medium having instructions thereon. The instructions, when executed by a computer, cause the computer to perform operations. The operations comprise separating a first view of a time series waveform into an unchanging intrinsic component and a changeable parameterized component. The operations comprise replacing a first parameter of the changeable parameterized component associated with the first view with a second parameter associated with a second view of the time series waveform. The operations changing the first view to the second view based on the unchanging intrinsic component and the changeable parameterized component with the second parameter.

Some aspects of the present techniques include a system for changing a first view of a time series waveform to a second view. The system comprises one or more processors and/or other components. The one or more processors are configured to separate the first view of the time series waveform into an unchanging intrinsic component and a changeable parameterized component. The one or more processors are configured to replace a first parameter of the changeable parameterized component associated with the first view with a second parameter associated with the second view. The one or more processors are configured to change the first view to the second view based on the unchanging intrinsic component and the changeable parameterized component with the second parameter.

Note that while the present disclosure focuses on changing views (e.g., by rotation, projection, and/or other techniques) of cardiac time series waveforms, the principles described herein may be applied for changing views of other time series waveforms including but not limited to time series waveforms associated with cardioid microphones (e.g., to improve microphone pattern detection); point-source (limited-source) sensors for radiating loop antennas; single-source Hall-effect sensors (magnetometers) to determine field lines of a remote magnetic source, and/or to determine position and orientation of resonant (contactless) charging devices to improve charging coil alignment (dynamic electric vehicle charging (DEVC); camera (quality) sensor of crankshafts, camshafts, wind turbines, and/or anything else spinning in three dimensional (3D) space; geolocation sensing of an individual's smartphone traveling on a two dimensional (2D) plane (e.g., ground) from a point source (e.g., a Wi-Fi tower); orbital mechanics of remote planetary systems from a limited field of view; photoacoustic spectroscopy; and/or other applications.

BRIEF DESCRIPTION OF THE DRAWINGS

The above-mentioned aspects and other aspects of the present techniques will be better understood when the present application is read in view of the following figures in which like numbers indicate similar or identical elements:

FIG. 2A shows an example of an ECG QRS complex with an R-pattern: monophasic with an upward deflection.

FIG. 2B shows an example of an ECG QRS complex with an Rs-pattern: biphasic waveform with an upward deflection followed by a relatively small downward deflection.

FIG. 2C shows an example of an ECG QRS complex with an RS-pattern: biphasic waveform with an upward deflection followed by a downward deflection.

FIG. 2D shows an example of an ECG QRS complex with an rS-pattern: biphasic waveform with a relatively small upward deflection followed by a downward deflection.

FIG. 2E shows an example of an ECG QRS complex with a Q-pattern: monophasic waveform with a downward deflection.

FIG. 2F shows an example of an ECG QRS complex with an Qr-pattern: biphasic waveform that starts with a downward deflection followed by a relatively small upward deflection.

FIG. 2G shows an example of an ECG QRS complex with a QR-pattern: biphasic waveform that starts with a downward deflection followed by a upward deflection.

FIG. 2H shows an example of an ECG QRS complex with a qR-pattern: biphasic waveform that starts with a relatively small downward deflection followed by an upward deflection.

FIG. 4A shows an example time series waveform $x(\alpha_0, t) = \sin(\alpha_0 t) u(t)$.

FIG. 4B shows an intrinsic component $(u(t))$ of $x(\alpha_0, t)$.

FIG. 4C shows a parametrized component $(\sin(\alpha_0 t))$ of $x(\alpha_0, t)$.

FIG. 4D shows the product of the sine wave $\sin(\alpha_1 t)$ and the same intrinsic component $u(t)$ as that in $x(\alpha_0, t)$.

FIG. 4E shows the intrinsic component $u(t)$ to be used in $x(\alpha_0, t)$, the same $u(t)$ as that in $x(\alpha_0, t)$.

FIG. 4F shows the sine wave $\sin(\alpha_1 t)$, with frequency $\alpha_1$.

FIG. 8A shows a first view to second view changed (e.g., projected) waveform from an original (first view of the) waveform of $\alpha_0 = 0.8$, but projected with an incorrect assumed frequency of $\hat{\alpha}_0 = 0.8(1+0)$.

FIG. 8B shows the projected waveform of an original waveform of $\alpha_0 = 0.8$, but projected with an incorrect assumed frequency of $\hat{\alpha}_0 = 0.8(1+0.001) = 0.8008$.

FIG. 8C shows the projected waveform of an original waveform of $\alpha_0 = 0.8$, but projected with an incorrect assumed frequency of $\hat{\alpha}_0 = 0.8(1+0.005) = 0.804$.

FIG. 8D shows the projected waveform of an original waveform of $\alpha_0 = 0.8$, but projected with an incorrect assumed frequency of $\hat{\alpha}_0 = 0.8(1+0.01) = 0.808$.

FIG. 12A shows measurement of pre-ejection period (PEP) for lead I of an ECG.

FIG. 12B shows measurement of PEP for lead II of an ECG.

FIG. 12C shows measurement of PEO for lead III of an ECG.

FIG. 12D shows measurement of PEP for the same lead I of an ECG as that shown in FIG. 12A, with its QRS projected to a monophasic waveform.

FIG. 12E shows measurement of PEP for the same lead II of an ECG as that shown in FIG. 12B, with its QRS projected to a monophasic waveform.

FIG. 12F shows measurement of PEP for the same lead III of an ECG as that shown in FIG. 12C, with its QRS projected to a monophasic waveform.

FIG. 13A shows the QRS of an ECG with left bundle branch block (LBBB).

FIG. 13B shows the same ECG as that shown in FIG. 13A, with its QRS projected to a monophasic waveform.

FIG. 15 illustrates measurement of T-wave to QRS amplitude ratio with associated projections.

FIG. 15A shows conventional measurement of T-wave to QRS amplitude ratio with leads V2, V3, and V4 of an ECG.

FIG. 15B shows a single-lead ECG (lead V2 of the same ECG shown in FIG. 15A) with its QRS projected to a monophasic waveform and its T-wave projected to a monophasic waveform.

FIG. 15C shows a single-lead ECG (lead V2 of the same ECG shown in FIG. 15A) with its QRS projected to a biphasic waveform and its T-wave projected to a monophasic waveform.

Figure 1:
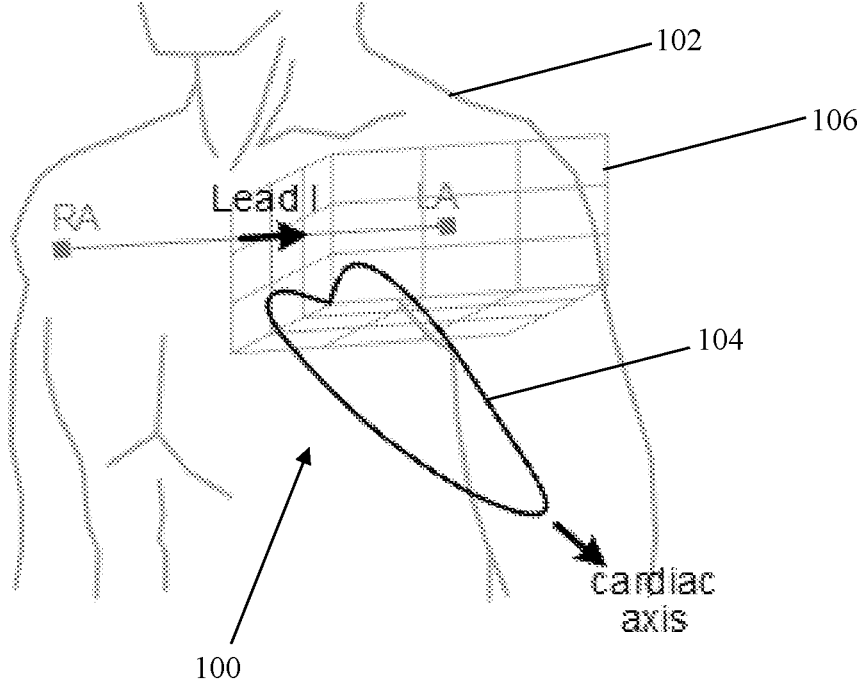
FIG. 1 shows the QRS complex of an electrocardiogram (ECG) in 3-dimensional (3D) space, and two distinct one-dimensional (1D) views (Lead I and cardiac axis) of this 3D waveform.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the field of ECG time series waveforms. The inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

A time series waveform provides a one-dimensional (1D) viewpoint of a trajectory. When the trajectory spans multiple dimensions in physical space or state space, multiple time-series waveforms observed from various viewpoints of the trajectory may improve the observation of the trajectory. For example, the electrical activity of the heart may be described as a trajectory in three-dimensional (3D) space. To observe this 3D trajectory, a conventional 12-lead electrocardiogram (ECG) displays 12 individual ID viewpoints of the trajectory, in the form of 12 time series waveforms acquired from multiple electrodes arranged on the body surface. The most prominent feature of every heartbeat in the ECG is the QRS complex waveform (QRS). The QRS represents the rapid electrical depolarization of the ventricles of the heart, resulting in heart muscle contraction that provides the pumping action of the heart. FIG. 1 shows an example of the trajectory 100 of the QRS of an ECG relative to the human torso 102 as depicted as a loop 104 in 3D space 106. FIG. 1 also illustrates two distinct one-dimensional (1D) views (Lead I and cardiac axis) of this 3D waveform, along with right arm (RA) and left arm (LA) leads for an ECG.

Figure 2:
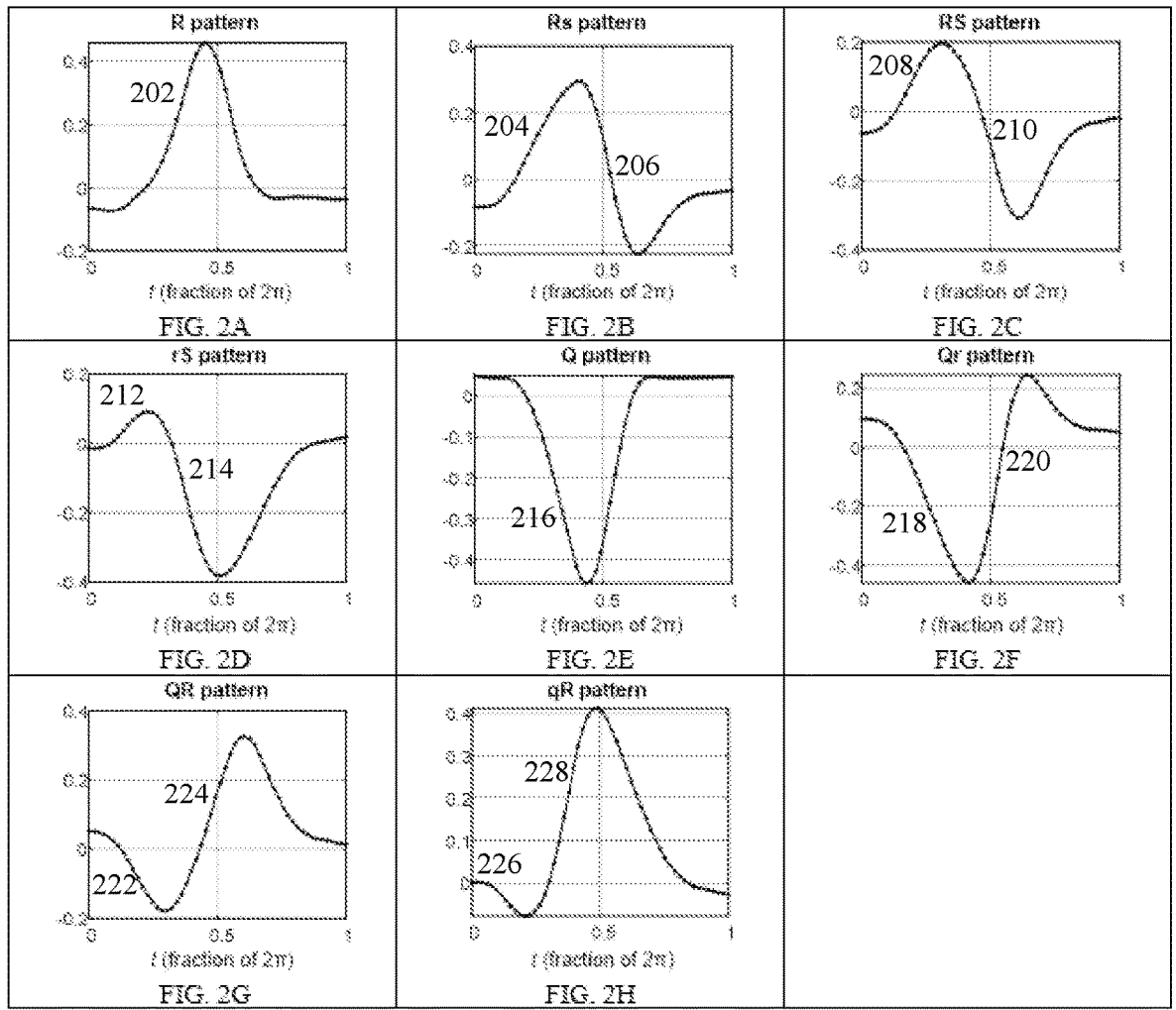
FIG. 2 illustrates examples of possible QRS ECG waveform patterns.

A QRS waveform of an ECG generally appears as a deflection away from a relatively static baseline. The waveform may be one of a single deflection (monophasic), two deflections (biphasic), or multiple deflections (multiphasic). The waveform may begin with an upward deflection or a downward deflection. For example, in the QRS of the ECG, a waveform can be described as belonging to various patterns. FIG. 2 illustrates examples of possible QRS ECG waveform patterns. FIG. 2A shows an example of an ECG QRS complex with an R-pattern: monophasic with an upward deflection 202. FIG. 2B shows an example of an ECG QRS complex with an Rs-pattern: biphasic waveform with an upward deflection 204 followed by a relatively small downward deflection 206. FIG. 2C shows an example of an ECG QRS complex with an RS-pattern: biphasic waveform with an upward deflection 208 followed by a downward deflection 210. FIG. 2D shows an example of an ECG QRS complex with an rS-pattern: biphasic waveform with a relatively small upward deflection 212 followed by a downward deflection 214. FIG. 2E shows an example of an ECG QRS complex with a Q-pattern: monophasic waveform with a downward deflection 216. FIG. 2F shows an example of an ECG QRS complex with an Qr-pattern: biphasic waveform that starts with a downward deflection 218 followed by a relatively small upward deflection 220. FIG. 2G shows an example of an ECG QRS complex with a QR-pattern: biphasic waveform that starts with a downward deflection 222 followed by a upward deflection 224. FIG. 2H shows an example of an ECG QRS complex with a qR-pattern: biphasic waveform that starts with a relatively small downward deflection 226 followed by an upward deflection 228.

The waveforms shown in the examples in FIG. 2A-2H are each distinct 1D projections of the same 3D trajectory of the QRS waveform of the ECG shown in FIG. 1. These individual waveforms describe the same 3D trajectory from eight different viewpoints. In cases where only one waveform, or one viewpoint, is provided, such as with an ECG provided by a smartwatch or other similar sensor, it would be a severely limited observation of the 3D trajectory shown in FIG. 1.

In multi-channel ECG interpretation, there are heart diseases or disorders that may be better observable given multiple viewpoints of the 3D trajectory of the QRS. But if only a single-channel viewpoint or waveform is provided, the observation of the 3D trajectory will be limited. A limited observation of the QRS in 3D may result in a missed detection of an ST elevation associated with myocardial infarction, of a deep Q-wave associated with myocardial infarction, of a bimodal shape of the QRS associated with bundle branch block, etc. Therefore, a need exists for the ability to project of a time series waveform from one viewpoint to other viewpoints for the purpose of improving observation of a multi-dimensional trajectory.

Advantageously, the present systems and methods provide for changing (e.g., projecting, rotating, and/or other changing) a first view of a time series waveform into a different view of the time series waveform by changing a parametrized component of the waveform. The change is based on the recognition that a time series waveform may be decomposed into an unchanging intrinsic component and a changeable parametrized component for a given parameter. The change from one view to another view is achieved by replacing the original value of the given parameter of the parametrized component with a different value associated with the second view, while holding the intrinsic component unchanged. The present systems and method make it possible to take a single-channel ECG and create a projection along a planar QRS loop that is more favorable for morphologic interpretation.

As described in more detail below, the present systems and methods are configured to estimate or otherwise determine a value of the parameter of the parametrized component from a first view of a time series waveform (e.g., by measuring the period of the first view of the waveform by finding the interval to the first zero-crossing of the waveform). The present systems and methods are configured to mitigate potential singularities (e.g., by identifying near-singularity segments, and by setting these near-singularity segments aside to be computed later using methods of alternative computation such as interpolation of segments of the projected waveform that are not near singularities, functional approximation near singularities, etc.). The present systems and methods are configured to mitigate inexact parameter estimates (e.g., by perturbation including testing changing waveforms with trial parameters in a neighborhood of the estimated parameter to find the parameter with the least amount of discontinuity in the resultant projected waveform, and measuring discontinuity by finding the maximum third derivative throughout the entire projected waveform, measuring the slopes only near singularities of the projected waveform, etc.). The present systems and method are configured to extend an optimized changed waveform to other waveforms by converting waveforms into waveforms of optimized patterns, and after changing a waveform to a second view, reversing part of the conversion, if necessary, to arrive at a final second view of the waveform.

The operations described herein may be performed with a software program, a computer, an electrocardiograph, a wearable device, an electrical circuit, a data acquisition module, a waveform converter, a combination thereof, and/ or other components. Operations may be performed by a system comprising a signal amplifier for obtaining a raw ECG from a subject, a data acquisition module for converting the raw ECG into a raw digital ECG, a waveform converter for projecting the ECG waveform, and/or other components. Operations may be performed by embedded software for conventional ECG devices, such as the Holter ECG and the 12-lead ECG, as a waveform converter for projecting the ECG waveform to provide more viewpoints of cardiac electrical activity, and/or other components.

The systems and methods described herein may be configured for improving automated or human interpretation of an ECG waveform for the following observations and any associated heart diseases or disorders, including but not limited to: arrival time of peak cardiac depolarization; monophasic morphology of a biphasic QRS waveform; ST elevation, associated with myocardial infarction; deep Q-wave, associated with myocardial infarction; QRS onset in the measurement of QT interval, associated with proar-rhythmic risk; QRS onset and offset in the measurement of QRS interval, associated with bundle branch blocks or heart remodeling; abnormalities in the shape of the QRS, associated with bundle branch blocks, Wolff-Parkinson-White syndrome, abnormalities in serum electrolyte concentration, hypothermia, and/or supraventricular tachycardia; and/or other cardiovascular diseases and/or conditions.

Figure 3:
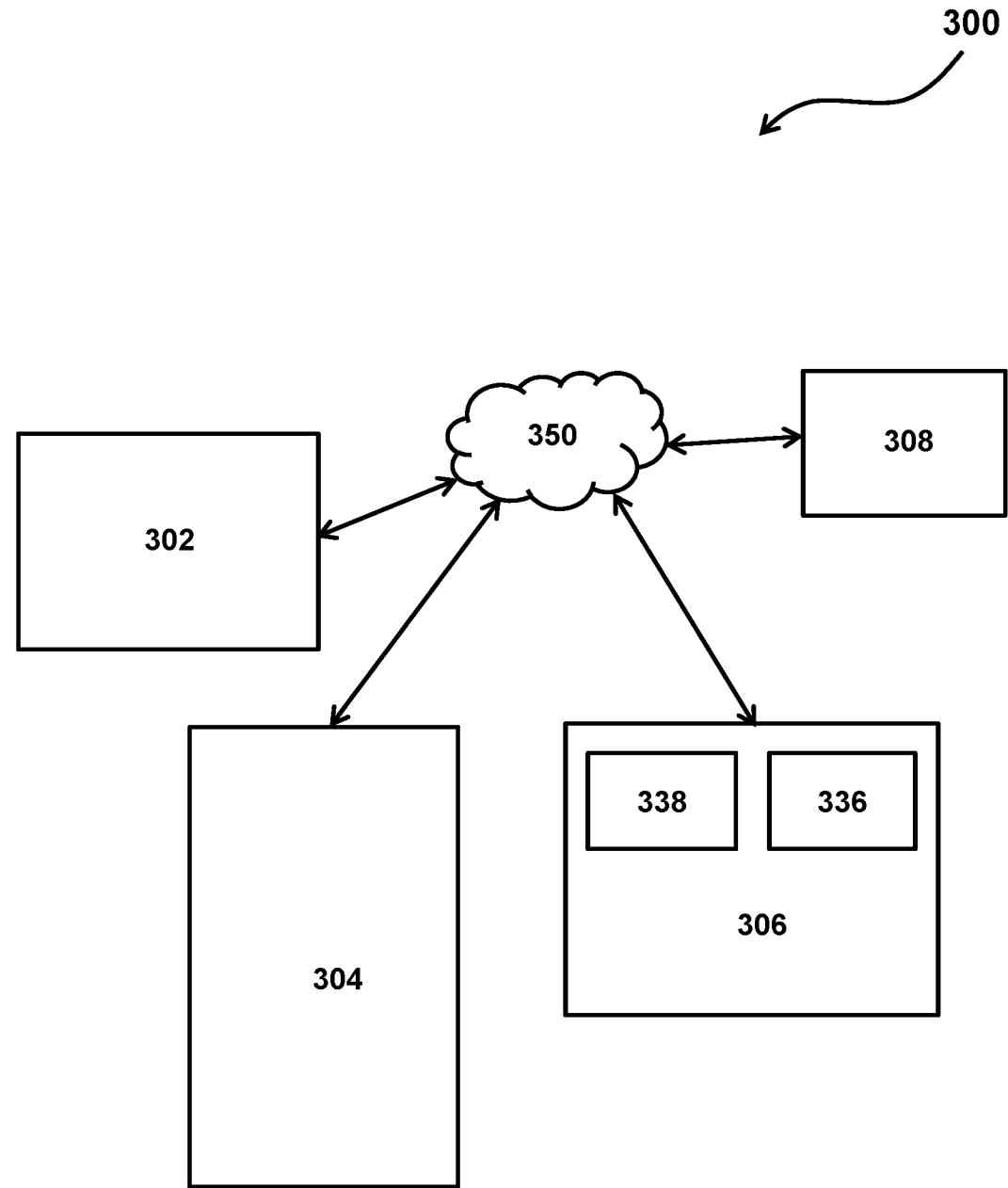
FIG. 3 provides a schematic illustration of a system configured for changing a first view of a time series waveform to a second view.

For example, FIG. 3 provides a schematic illustration of a system 300 configured for changing a first view of a time series waveform to a second view. FIG. 3 illustrates an embodiment of system 300 comprising an ECG system 302, one or more processors 304, one or more computing devices 306, external resources 308, a network 350, and/or other components. Each of these components is described in turn below.

ECG system 302 is configured to generate one or more output signals conveying ECG information for a subject. ECG system 302 may comprise an electrocardiograph, a wearable device, an electrical circuit, a data acquisition module, a computer, and/or other components. ECG system 302 may comprise a signal amplifier for obtaining a raw ECG from a subject, a data acquisition module for converting the raw ECG into a raw digital ECG, and/or other components. Operations of ECG system 302 may be performed by embedded software for conventional ECG devices. ECG system 302 may comprise a Holter ECG, a 12-lead ECG, and/or other ECGs. ECG system 302 may be deployed in a patch, a wristband, a watch, a garment, exercise equipment, and/or other devices, for example. ECG system 302 may be configured to be worn at or near the heart of the subject, for example. In some embodiments, ECG system 302 may be and/or include a necklace, a chest strap, a shirt, a vest, and/or any other wearables configured such that system 300 can function as described herein.

One or more processors 304 are configured to provide information processing capabilities in system 300. One or more processors 304 may comprise or be controlled by a software program. One or more processors 304 may be included in a computer such as computing device 306, for example. One or more processors 304 may comprise a waveform converter for projecting an ECG (e.g., QRS) waveform to provide more viewpoints of cardiac electrical activity, and/or other components.

One or more processor(s) 304 may include one or more of a digital processor, an analog processor, a digital circuit designed to process information, an analog circuit designed to process information, a state machine, and/or other mechanisms for electronically processing information. In some embodiments, a processor 304 may be included in and/or otherwise operatively coupled with ECG system 302, computing device 306, and/or other components of system 300. Although one or more processors 304 are shown in FIG. 3 as a single entity, this is for illustrative purposes only. In some implementations, processor(s) 304 may include a plurality of processing units. These processing units may be physically located within the same device (e.g., ECG system 302, computing device 306, etc.), or processor(s) 304 may represent processing functionality of a plurality of devices operating in coordination (e.g., a processor located within ECG system 302 and a second processor located within computing device 306). Processor(s) 304 may be configured to execute one or more computer program components. Processor(s) 304 may be configured to execute the computer program component by software; hardware; firmware; some combination of software, hardware, and/or firmware; and/or other mechanisms for configuring processing capabilities on processor(s) 304.

Processor(s) 304 are configured to change a first view of a time series waveform to a second view. Changing may comprise projecting, rotating, and/or other operations. The first view of the time series waveform may be generated based on a single channel electrocardiogram (ECG) signal from ECG system 302 and/or other sources. In some embodiments, the time series waveform comprises a mono-phasic or biphasic single channel QRS waveform associated with an ECG. In some embodiments, the time series waveform comprises a projection of a QRS loop. The second view of the time series waveform may be a projection along a planar QRS loop that is more favorable for morphologic interpretation compared to the first view. Processor(s) 304 are configured to change the first view to the second view based on the unchanging intrinsic component and the changeable parameterized component with the second parameter. In some embodiments, the separating, replacing, changing, and/or other operations described herein are performed to determine a center of a QRS complex, determine a width of the QRS complex, and/or determine ST elevation/ depression and/or other cardiovascular diseases and/or conditions.

Processor(s) 304 are configured to separate the first view of the time series waveform into an unchanging intrinsic component and a changeable parameterized component. For example, to allow for different views of a single time-series waveform, the time series waveform (x) over a span of time (t) spanning a $2\pi$ period be separatable (or decomposable) into two components: an intrinsic component, u(t), that remains unchanged, and a parametrized component, v($\alpha$, t), of parameter $\alpha$, that, if changed, may provide a different viewpoint of the waveform. The general form of this time-series waveform may be written as:

$$x(\alpha,t)=v(\alpha,t)u(t).$$

In some embodiments, the unchanging intrinsic component is upright and monophasic. In some embodiments, the parameterized component comprises a sinusoidal function and the first and second parameters comprise different frequencies of the sinusoidal function. The sinusoidal function may be a sine function or a cosine function. For example, one way to represent the parametrized component is with a sinusoid function such as the sine or the cosine function, with the frequency of the sinusoid function as the parameter $\alpha$. In some embodiments, the parameterized component comprises a Taylor series expansion and the first and second parameters (e.g., different $\alpha$'s) comprise different Taylor series.

One method of parametrizing with a sinusoid function is to use a sine function for the sinusoid: $v(\alpha, t)=\sin(\alpha t)$, over time t spanning 0 and $2\pi$. Using the sine function, the waveform may be written as:

$$x(\alpha,t)=\sin(\alpha t)u(t),t\in [0,\ 2\pi].$$

Figure 4:
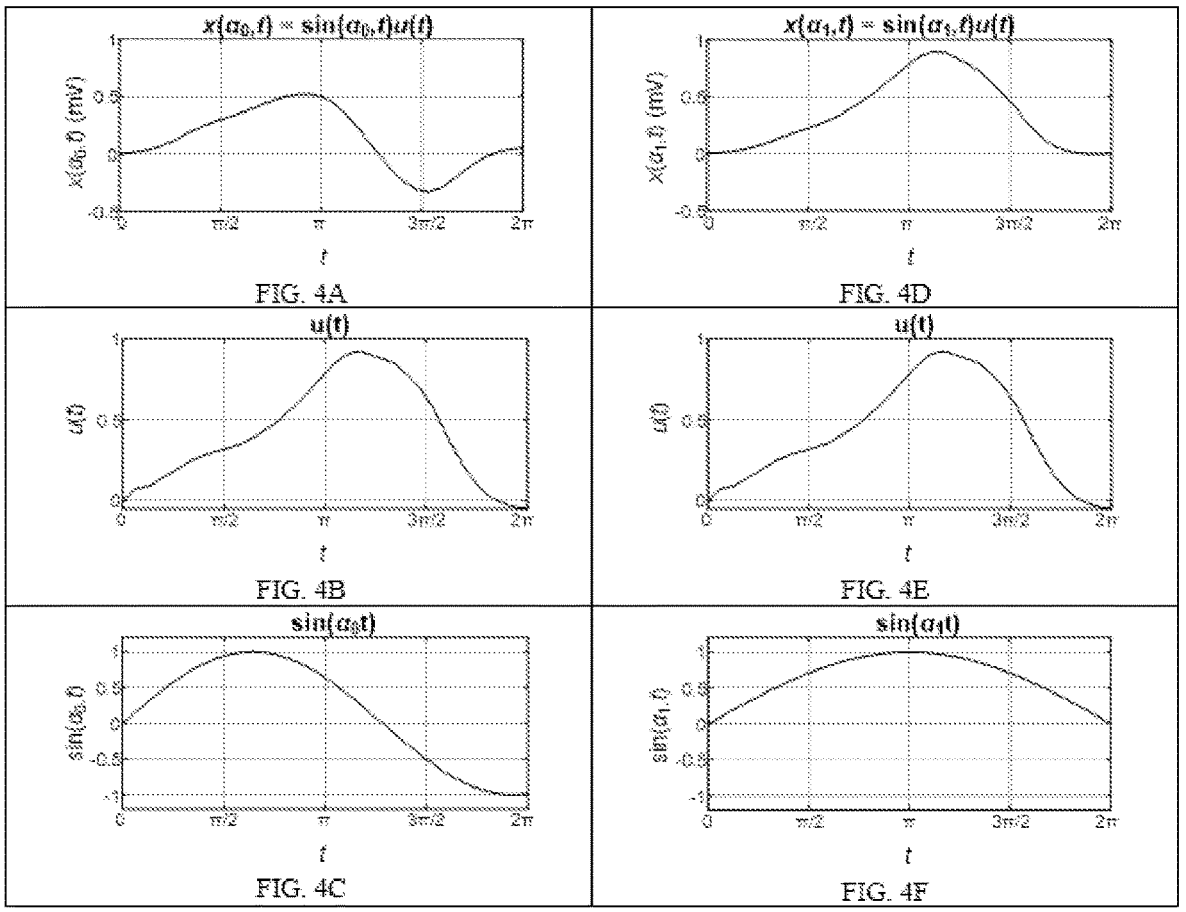
FIG. 4 illustrates aspects of various waveforms.

FIG. 4 illustrates aspects of various waveforms. FIG. 4A shows an example QRS waveform $x(\alpha_0,\ t)$. By assuming that the waveform is decomposable, it is possible to find an u(t) (shown in FIG. 4B) and a $\sin(\alpha_0 t)$ with a frequency $\alpha_0$ (shown in FIG. 4C) such that $x(\alpha_0,\ t)=\sin(\alpha_0 t)u(t)$ for $t\in [0, 2\pi]$, where u(t) represents the intrinsic component of this QRS, which remains unchanged throughout the projection process, and $\sin(\alpha_0 t)$ represents the parametrized component of this QRS (time series waveform).

In the example of FIG. 4A, $\alpha_0=0.78$ and both $x(\alpha_0, t)$ and $\sin(\alpha_0 t)$ are of a biphasic pattern. On the other hand, if the projected (e.g., changed) waveform is to be upright and monophasic, then a desired sinusoid may be chosen to be $\sin(0.5t)$ (shown in FIG. 4F), which is upright and monophasic in the span $t\in [0, 2\pi]$. If the parametrized component of the first view (e.g., original) waveform $\sin(\alpha_0 t)$ is replaced by $\sin(\alpha_1 t)$ with $\alpha_1=0.5$, then the projected (e.g., changed) waveform $\sin(\alpha_1 t)u(t)$ would continue to retain the intrinsic component u(t) (FIG. 4E), while providing a projected waveform (FIG. 4D) that is upright and monophasic.

Another method of parametrizing with a sinusoid function is to use a cosine function for the sinusoid: $v(\alpha, t)=\cos(\alpha t)$ over a time span between $-\pi$ and $\pi$. Using the cosine function, the waveform may be written as:

$$x(\alpha,t)=\cos(\alpha t)u(t),t\in [-\pi,\pi].$$

By separating a time-series waveform into an unchanging intrinsic component and a parametrized component, a first view of the waveform may be changed to another (e.g., a second) view of the waveform by replacing its parametrized component. Processor(s) 304 are configured to replace a first parameter of the changeable parameterized component associated with the first view with a second parameter associated with the second view.

In some embodiments, replacing the first parameter with the second parameter comprises parameterized component division. For example, using a first view of a time series waveform of the sine parametrization form $x(\alpha_0, t)=\sin(\alpha_0 t)$ u(t), the target second view of the waveform $x(\alpha_1,\ t)=\sin$ $(\alpha_1 t)u(t)$ may be estimated by scaling with the ratio of the two sine functions according to (where $\hat{x}$ indicates an estimate of x):

$$\hat{x}(\alpha_1,\ t) = \frac{\sin(\alpha_1 t)}{\sin(\alpha_0 t)}x(\alpha_0,\ t).$$

Figure 5:
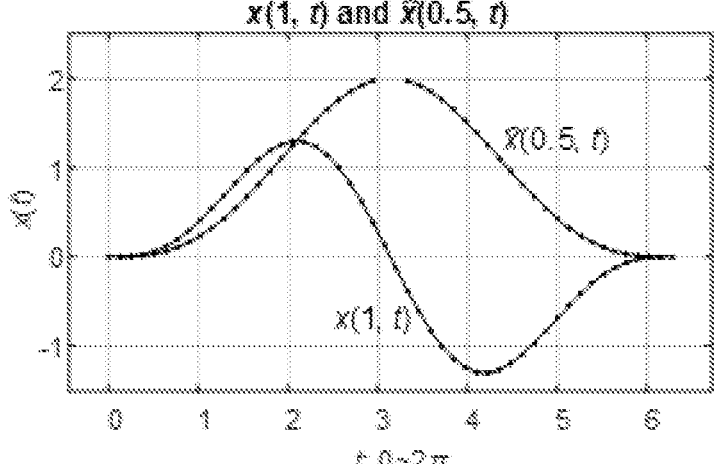
FIG. 5 shows an example of an original waveform with $\alpha = 1.0$, and the projected waveform with $\alpha = 0.5$, both waveforms having the same intrinsic component $u(t)$.

FIG. 5 illustrates an example of projection by sine division of an original waveform with $\alpha_0=1$ to a projected waveform with $\alpha_1=0.5$, computed as follows:

$$\hat{x}(0.5,\ t) = \frac{\sin(0.5t)}{\sin(t)}x(1,\ t).$$

FIG. 5 shows x(1, t) and $\hat{x}(0.5,\ t)$, sampled over 50 samples over $t\in [0, 2\pi]$, without samples of t where $|\sin(t)|<0.1$, where sin(t) is near zero. Depending on the sampling rate and the original (e.g., first view) and the target (e.g., second view) frequencies, and/or other factors, changing time-series waveforms by parametrized component replacement may require further considerations such as:

(1) Estimation of Waveform Parameters—original waveforms (e.g., first views of time series waveforms) may have an unknown parameter for their parametrized components. Estimation of the parameter, $\alpha_0$, of a parametrized component may be necessary prior to parametrized component replacement.

(2) Mitigation of Singularities—replacement of the value of the parameter of the parametrized component may result in singularities at segments of the parametrized component that are near-zero. A mitigation of singularities may be necessary for this replacement.

(3) Mitigation of Inexact Parameter Estimates—an inexact estimate of the original (first view of the) time series waveform parameter may cause unpredictable discontinuities near the singularities. A mitigation of inexact parameter estimates may be necessary to find a more exact parameter.

(4) Extending Optimized Projection to All Waveforms—replacement of parameter values of the parametrized component may be optimal for projecting original waveforms with certain patterns, and not for other patterns. Given original (first views of) waveforms of other patterns, it may be necessary to convert these original waveforms into one of the optimal patterns prior to parametrized component replacement.

Parameter Determination

Figure 6:
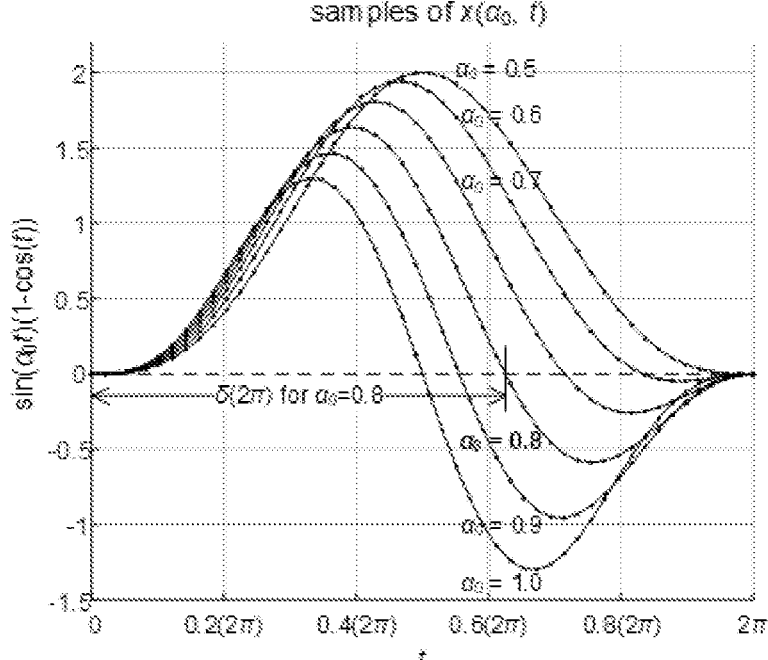
FIG. 6 shows $x(\alpha_0, t) = \sin(\alpha_0 t)(\alpha - \cos t)$ (which can be written more generally as $x(\alpha, t) = A \sin(\alpha t)(1 - \cos \beta t)$) of various frequencies $\alpha_0 \in [0.5, 1.0]$.

Given some original (e.g., first view of a) time series waveform $x(\alpha_0, t)$ where the parameter $\alpha_0$ is unknown, it is necessary to find some $\hat{\alpha}_0$ to estimate $\alpha_0$ ($\hat{\alpha}_0$ indicates an estimate of $\alpha_0$, where $\alpha_0$ is the "true" alpha (parameter) of the original waveform, and can never really be exactly found, only estimated to a certain numerical precision, or estimated to have a sufficient precision to produce an error below a threshold (such as the threshold described below)). FIG. 6 shows original (e.g., first views of) waveforms of a sine parametrization form $x(\alpha_0, t)=\sin(\alpha_0 t)u(t)$ (which can be thought of more generally as $x(\alpha, t)=A \sin(\alpha t)(1-\cos \beta t)$) with the same intrinsic component u(t) but different parametrized components $\sin(\alpha_0 t)$. FIG. 6 shows that different values of $\alpha_0$ result in different periods of $x(\alpha_0, t)$ over $t\in [0, 2\pi]$. Processor(s) 304 are configured to estimate $\alpha_0$ using a period length of the original waveform and/or other information.

For example, in some embodiments, processor(s) 304 (FIG. 3) may be configured such that the first parameter of the changeable parameterized component associated with the first (e.g., original) view of a time series waveform may be determined based on a first zero crossing of the time series waveform. In the example of sine function parametrization, the location of the first zero-crossing of a first view of a (e.g., an original) waveform after the start of the waveform is the halfway point of a full period $(2\pi)$. Let $\delta$ be defined as the proportion of $2\pi$ of the first zero-crossing of $x(\alpha_0, t)$ after $t=0$. If the original waveform spans $t \in [0, 2\pi]$, then the first zero-crossing occurs at $t=\delta(2\pi)$. The first zero-crossing after the start of a sine wave also occurs where $\sin(\hat{\alpha}_0 t)=\sin(\pi)$. Hence the first zero-crossing occurs at $\hat{\alpha}_0 t=\hat{\alpha}_0 \delta(2\pi)=\pi$, or:

$$\hat{\alpha}_0 = \frac{1}{2}\delta.$$

For example, for the $\sin(0.8t)$ curve of FIG. 6, the first zero-crossing after the start of the waveform occurs at $t=0.625(2\pi)$, hence $\delta=0.625$. Using the frequency estimation, $\hat{\alpha}_0 = \frac{1}{2}\delta = 0.8$, which is an estimate of the original (first view) $\alpha_0$ of 0.8.

Mitigation of Singularities

When the parametrized component of the original (e.g., first view of a) time series waveform is at or near zero, division by this parametrized component may approach numerical singularity. Processor(s) 304 may be configured to mitigate potential singularities or near-singularities caused by parameterized component division by identifying segments of the second view of the time series waveform that comprise the potential singularities or near-singularities, applying an alternative computation to change the first view to the second view at these potential singularity or near-singularity segments, and/or other operations. For example, using the sine parametrization, processor(s) 304 may be configured such that the following rules may be applied:

if a segment is identified as being near singularity, then compute $$\hat{x}(\alpha_1, t) = \frac{\sin(\alpha_1 t)}{\sin(\hat{\alpha}_0 t)} x(\hat{\alpha}_0, t);$$

and if a segment is not identified as being near singularity, then use an alternative computation for projection.

The potential singularities or near singularities may be identified by processor(s) 304 based on a threshold on sines of frequencies of the first view of the time series waveform and/or by other operations. For example, one method used by processor(s) 304 for identifying near-singularity segments in an original (e.g., a first view of a) time series waveform segment is to create a threshold $(\theta)$ such that, in the example of sine parametrization, if $|\sin(\hat{\alpha}_0 t)| < \theta$, then the segment is near-singularity, otherwise it is not. Another method of identifying near-singularity segments in an original waveform segment is to create a threshold $(\theta)$ such that, in the example of sine parametrization, if $|x(\alpha_0, t)/\sin(\hat{\alpha}_0 t)| \geq \theta$, then the segment is near-singularity, otherwise it is not.

In some embodiments, the alternative computation may be or include interpolation of the identified segments using the second view of the time series waveform at segments that are not near-zero, as determined by parametrized component replacement. For example, processor(s) 304 may be configured for interpolation of these segments using the changed waveform at segments that are not near-zero, that have been computed by parametrized component replacement. A variety of linear or nonlinear methods may be employed to perform this interpolation. In the example of sine parametrization, a cubic spline interpolation of the segments of the projected waveform computed by sine-division at $\{\hat{x}(\alpha_1, t) \| |\sin(\alpha_0 t)| \geq \theta\}$ may be used to compute the near-singularity segments at $\{\hat{x}(\alpha_1, t) \| |\sin(\alpha_0 t)| < \theta\}$, for example.

Figure 7:
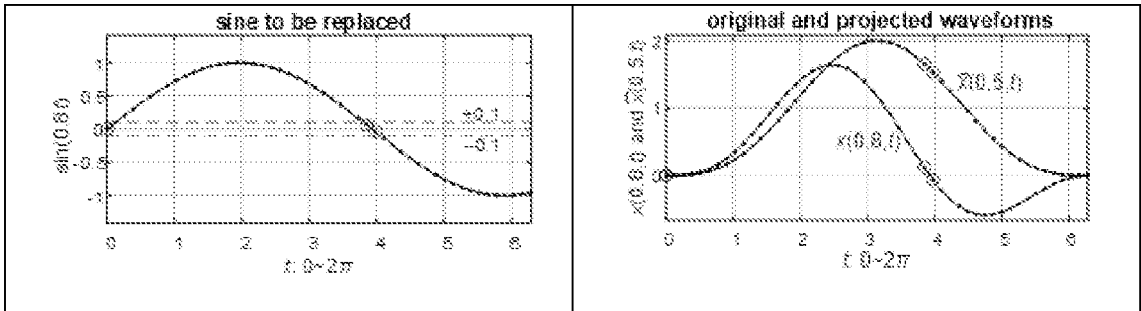
FIG. 7A shows $\sin(0.8t)$ over $t \in [0, 2\pi]$, sampled over 50 samples, with values within 0.1 of zero circled.
FIG. 7B shows a first view of a (e.g., an original) time series waveform with $\hat{\alpha}_0 = 0.8$, the changed waveform with $\alpha_1 = 0.5$, with the corresponding in FIG. 7A circled.

To illustrate the method of interpolation, assume a first view of a waveform to be changed comprises $x(\alpha_0, t)$, $\alpha_0=0.8$. FIG. 7A shows the parametrized component sin $(0.8t)$ over $t \in [0, 2\pi]$, sampled over 50 samples, with near-singularity values identified by $|\sin(\alpha_0 t)| < \theta$, $\theta=0.1$, denoted with circles. FIG. 7B shows the original waveform with $\hat{\alpha}_0=0.8$, the projected waveform with $\alpha_0=0.5$, with the corresponding in FIG. 7A circled. To perform projection with mitigation of singularities, the points that are not near-singularity may be determined first by sine-division. Afterwards, the near-singularity points (circled) may be determined using cubic spline interpolation of the points previously computed by sine-division, for example.

In some embodiments, processor(s) 304 (FIG. 3) are configured such that the alternative computation is performed using functional approximation, as the parametrized component with the second parameter approaches singularity. For example, various discontinuity smoothing schemes can be employed, including partitions of unity, as well as analytical approximations by using small-angle assumptions or by considering the limiting behavior of the parameterized components, and/or other schemes.

Mitigation of Inexact Parameter Estimates

Time series waveform segments of near-singularity may be identified based on the (original) parametrized component of the first view, which may be based on an estimate of its parameter $(\hat{\alpha}_0)$, for example. Inexact parameter estimates may shift the segments of near-singularity, causing discontinuities. In the example of a sine parametrization, a small inexactness in its frequency parameter $\hat{\alpha}_0 \neq \alpha_0$ when dividing by $\sin(\hat{\alpha}_0 t)$ may cause discontinuities in the changed—first view to second view (projected)—waveform. Inexactness of estimation $\varepsilon$ where $\hat{\alpha}_0 = (1+\varepsilon)\alpha_0$, may make it difficult to identify samples of $t$ where $\sin((1+\varepsilon)\alpha_0 t)$ is near zero for the mitigation of discontinuities near the singularities of $\sin(\hat{\alpha}_0 t)$.

Figure 8:
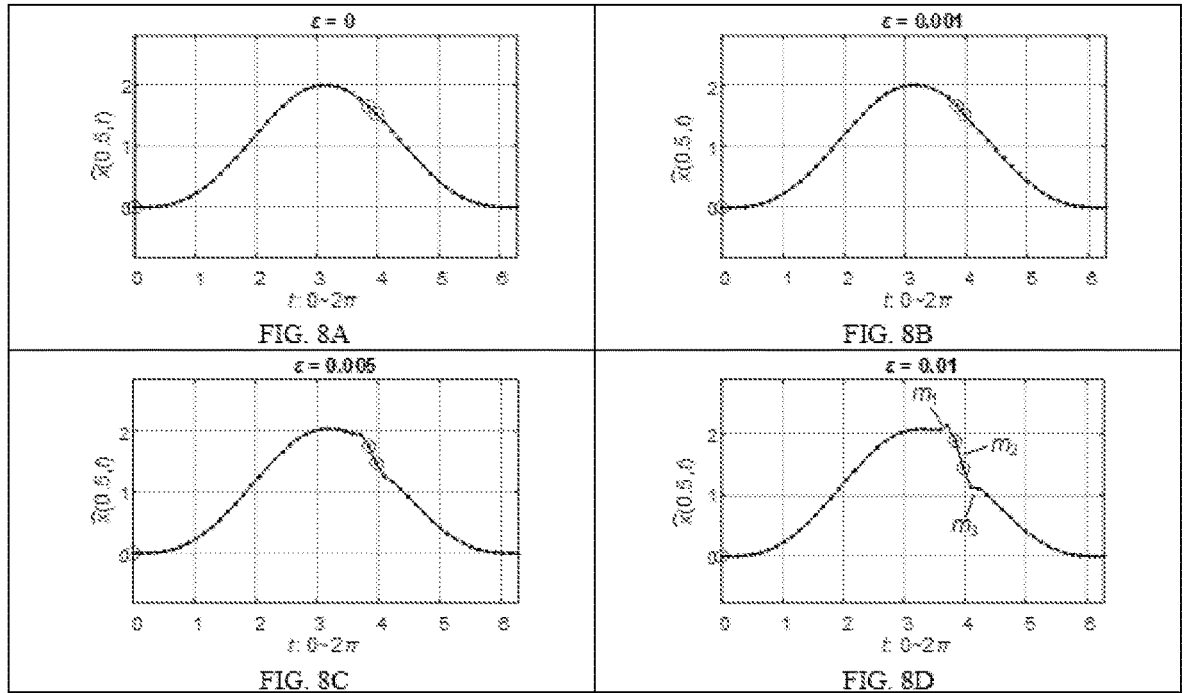
FIG. 8 shows the effect of error in estimated frequency of the first view in projection.

FIG. 8 shows the effect of error in estimated frequency of the first view in projection. FIGS. 8A, 8B, 8C, and 8D respectively show first view to second view time series waveform change (e.g., projection) from $x(0.8, t)$ to $\hat{x}(0.5, t)$ with added inexactness of $\varepsilon=0$, 0.001, 0.005, 0.01. The circled samples denote samples where $|\sin(\hat{\alpha}_0 t)| < 0.1$, and are interpolated. With increasing levels of $\varepsilon$, the projected waveform $\hat{x}(0.5, t)$ exhibits more pronounced discontinuities near the singularities. Ideally the waveform preceding, during, and following the singularity should be continuous and have as similar first derivatives as possible.

In some embodiments, processor(s) 304 (FIG. 3) are configured to mitigate inexact parameter determinations by perturbation and/or other methods. Perturbation may comprise testing different parameter values to determine which parameter value provides a best changed time series waveform continuity (or least discontinuity). For example, perturbation may comprise finding a parameter in a neighborhood of a parameter value estimate $\hat{\alpha}_0$ that provides the best projected waveform continuity, given the parameter estimate $\hat{\alpha}_0$ of the first view of the (e.g., the original) waveform by: searching for various trial parameter values $\alpha$ within $\hat{\alpha}_0 \pm \varepsilon$, $\varepsilon$ being a neighborhood size; and at each trial $\alpha$, determining a measurement of discontinuity $D_m$; such that the trial $\alpha$ that has the lowest discontinuity measurement will be the $\alpha_0$ to be used for changing the first view to the second view (e.g., for projection).

In some embodiments, processor(s) 304 (FIG. 3) may be configured such that discontinuity is determined by determining slopes of the time series waveform preceding, during, and following singularity or near-singularity segments. For example, for the first view to second view changed (e.g., projected) time series waveform shown in FIG. 8D, $m_1$ is the slope preceding the singularity, $m_2$ is the slope during the singularity, and $m_3$ is the slope following the singularity. A second derivative (e.g., acceleration) between the three slopes may be taken at each $$m(\alpha,k)=|(m_3-m_2)-(m_2-m_1)|,$$

and the discontinuity measurement, $D_m$ ($\alpha$), for each trial $\alpha$ may be the maximum m($\alpha$, k) among all near-singularity segments throughout the entire waveform.

Given the possibility that a frequency estimate $\hat{\alpha}_0$ may be near $\alpha_0$ but not exactly so, a better estimate may be found by testing values near $\hat{\alpha}_0$ for a frequency that minimizes $m_D$. For example, with an estimate $\hat{\alpha}_0$, a search may be conducted within $\hat{\alpha}_0 \pm \varepsilon$, $\varepsilon$=0.05, in steps of 0.001 for the minimum $D_m$. In the example where the ideal $\alpha_0$ is 0.8 with an inexactness of $\varepsilon$=0.01, the estimate is $\hat{\alpha}_0$=(1+$\varepsilon$)$\alpha_0$=(1.01)(0.8)=0.808.

Figure 9:
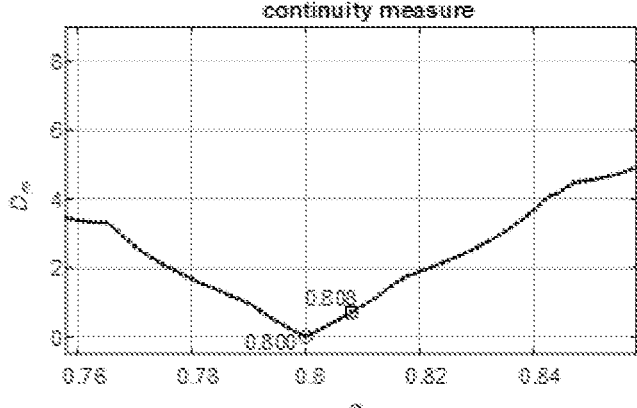
FIG. 9 shows values of a continuity measure $(D_m)$ of a search of $\alpha_0 \in (0.808 + [-0.05, 0.05])$ in the example shown in FIG. 8D.

FIG. 9 shows a search in the range of 0.808±0.05 in steps of 0.001 that finds the minimum $D_m$ at 0.800. The figure also shows that $D_m$ has a unique minimum within this search range.

In some embodiments, processor(s) 304 (FIG. 3) are configured such that discontinuity may be determined by determining a largest third derivative throughout the second view of the time series waveform at each trial parameter value. The largest third derivative may be found throughout the first view to second view changed (e.g., projected) time series waveform at each trial $\alpha$. For example, given a discrete-time waveform of length n, the amplitude of the third derivative may be written as:

$$m(\alpha,k)=|\hat{x}(\alpha,t(k))-3\hat{x}(\alpha,t(k-1))+3\hat{x}(\alpha,t(k-2))-\hat{x}(\alpha,t(k-3))|,$$

and the discontinuity measurement $D_m$ ($\alpha$) for each trial $\alpha$ is the maximum amplitude of the third difference throughout the entire waveform:

$$D_m(\alpha)=\max\{m\alpha a,k),k=4,5,\ldots,n\}.$$

Extending an Optimized First View to Second View Changed (Projected) Waveform to Other Waveforms Processor(s) 304 (FIG. 3) may be configured such that the operations described above may be extended to, and/or the time series waveform may be converted to, other waveform patterns by flipping a time axis, flipping a waveform axis, changing the parameter, and/or introducing a shift to the parameterized component of the first view of the time series waveform.

Waveform projection (e.g., changing from a first view to a second view) may only be optimal for certain patterns of an original (e.g., first view of the) waveform. For example, for the original waveform of a sine parametrization form $x(\alpha_1, t)=\sin(\alpha_0 t)u(t)$ where $t \in [0, 2\pi]$, there is only one singularity expected after the start of the waveform at $\alpha_1 t=\pi$. If the first wave of the waveform is not dominant, or if its first zero-crossing occurs at $\delta$<0.5, then there would be more than one singularity after the start of the waveform. Sine division with singularity mitigation is optimized for original waveforms where the first zero-crossing after the start of the waveform occurs at or after the halfway point ($\delta \geq 0.5$), or where the first wave "dominates" the waveform. Also, if the sine function is used to represent the parametrized component, then the first wave of the original waveform should be upright, as the first wave of $\sin(\alpha_0 t)$ is upright for any nonzero $\alpha_1$ for $t \geq 0$. Hence, waveform projection that uses sine-division as the projection method is optimized for original waveforms where the first wave is dominant and upright, belong to waveforms of the {R, Rs, RS} patterns. In addition to waveforms of the {R, Rs, RS} patterns, there are other waveforms that do not start with a dominant upright wave, such as the following sets of patterns:

{Q, Qr, QR} that start with a dominant downward wave (e.g., the Q-wave);

{qR} that has a dominant upright wave (e.g., the R-wave) but starts with a relatively small downward wave (e.g., the Q-wave); and {rS} that has a dominant downward wave that follows an upward wave (e.g., the S-wave) but starts with a relatively small upright wave (e.g., the R-wave)

Figures 10, 10A, 10B, 10C, 10D:
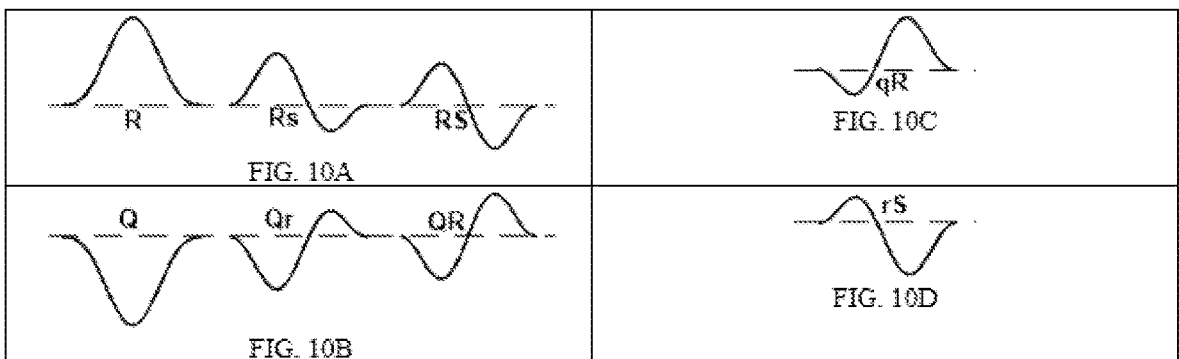
FIG. 10 shows waveforms with various patterns.
FIG. 10A shows waveforms of the set of {R, Rs, RS} patterns.
FIG. 10B shows waveforms of the set of {Q, Qr, QR} patterns.
FIG. 10C shows waveforms of the set of {qR} pattern.
FIG. 10D shows waveforms of the set of {rS} pattern.

By way of several examples, FIG. 10 shows waveforms with various patterns. FIG. 10A shows waveforms of the set of {R, Rs, RS} patterns, FIG. 10B shows waveforms of the set of {Q, Qr, QR} patterns, FIG. 10C shows waveforms of the set of {qR} patterns, and FIG. 10D shows waveforms of the set of {rS} patterns. The {Q, Qr, QR} patterns appear to be the {R, Rs, RS} patterns mirrored in waveform amplitude. The qR pattern appears to be the Rs pattern mirrored in time. And the rS pattern appears to be the Rs pattern mirrored in both waveform amplitude and in time.

One method of extending a first view to second view change (e.g., a projection) to other pattern waveforms is by converting the original (first view of a) time series waveform (x) to create a converted waveform (y) that is of the optimized patterns. In the example of sine parametrization, projection may be optimized for original waveforms of an {R, Rs, RS} pattern. For all sets of waveform patterns, the following two rules may be applied:

if $\delta \in [0, 0.5]$, flip the horizontal (time) axis and change $\alpha_0$ from $$\frac{1}{2\delta} \text{ to } \frac{1}{2(1-\delta)};$$

and after any horizontal flipping of the previous step, if the first wave of the waveform continues to be a downward wave, then flip the vertical (waveform) axis.

By exercising these two (and/or other) rules, the sets of waveform patterns described above may be converted by processor(s) 304 (FIG. 3) by way of vertical (waveform) axis flipping, horizontal (time) axis flipping, both axis flipping, or neither axis flipping:

If the original waveform is of {R, Rs, RS} patterns (shown in FIG. 10A): $\delta \in [0.5,1]$, hence horizontal axis flipping is not necessary, and $\alpha_0$ remains 1/(2$\delta$); and without horizontal axis flipping, the first wave of the waveform remains upward, hence vertical axis flipping is not necessary. If the original waveform is of {Q, Qr, QR} patterns (shown in FIG. 10B): $\delta \in [0.5,1]$, hence horizontal axis flipping is not necessary, and $\alpha_1$ remains 1/(2$\delta$), and without horizontal axis flipping, the first wave of the waveform remains downward, hence vertical axis flipping is necessary. If the original waveform is of the {qR} pattern (shown in FIG. 10C): $\delta \in [0, 0.5)$, hence horizontal axis flipping is necessary, and $\alpha_0$ is changed to 1/(2(1−$\delta$)); and with horizontal axis flipping, the first wave of the waveform becomes upward, hence vertical axis flipping is not necessary. If the original waveform is of the {rS} pattern (shown in FIG. 10D): $\delta \in [0, 0.5)$, hence horizontal axis flipping is necessary, and $\alpha_0$ is changed to $1/(2(1-\delta))$; with horizontal axis flipping, the first wave of the waveform becomes downward, hence vertical axis flipping is necessary.

One method used by processor(s) 304 of converting a waveform to the optimized patterns may be to flip the vertical and/or the horizontal axes of the entire original waveform (x), in order to convert the original waveform to a waveform y of an optimized pattern prior to projection.

Since a horizontal axis flipping reverses the time sequence of the waveform, the time sequence should be restored after projection. If the converted waveform (y) has not undergone horizontal flipping, then the projection of the original waveform ($\hat{x}$) will be the same as the projection of the converted waveform ($\hat{y}$): $\hat{x}(\alpha_1, t) = \hat{y}(\alpha_1, t)$. If the converted waveform (y) has undergone horizontal flipping, then the projection of the original waveform ($\hat{x}$) will be the horizontal flip of the projection of the converted waveform ($\hat{y}$). Given a time that spans $t \in [0, 2\pi]$, a horizontal flip would be $\hat{x}(\alpha_1, t) = \hat{y}(\alpha_1, 2\pi - t)$.

Given the original waveform x over $t \in [0, 2\pi]$ and its zero-crossing ratio ($\delta$), the method of flipping vertical and/or horizontal axes may be performed as follows:

No flipping, for original waveform of {R, Rs, RS} patterns $\alpha_0 = 1(2\delta)$ $y_0(\alpha_0, t) = x(\alpha_0, t)$ project $y_0(\alpha_0, t)$ from the original frequency $\alpha_0$ to the target frequency $\alpha_1$, to find $\hat{y}(\alpha_1, t)$ $\hat{x}(\alpha_1, t) = \hat{y}(\alpha_1, t)$ Flipping the vertical (waveform) axis, for original waveforms of {Q, Qr, QR} patterns $\alpha_0 = 1(2\delta)$ $y_V(\alpha_0, t) = -x(\alpha_0, t)$ project $y_V(\alpha_0, t)$ from the original frequency $\alpha_0$ to the target frequency $\alpha_1$, to find $\hat{y}(\alpha_1, t)$ $\hat{x}(\alpha_1, t) = \hat{y}(\alpha_1, t)$ Flipping the horizontal (time) axis, for original waveforms of {qR} pattern $\alpha_0 = 1/(2(1-\delta))$ $y_H(\alpha_0, t) = x(\alpha_0, 2\pi - t)$ project $y_H(\alpha_0, t)$ from the original frequency $\alpha_0$ to the target frequency $\alpha_1$, to find $\hat{y}(\alpha_1, t)$ $\hat{x}(\alpha_1, t) = \hat{y}(\alpha_1, 2\pi - t)$ Flipping both vertical and horizontal axes, for original waveforms of {rS} pattern $\alpha_0 = 1/(2(1-\delta))$ $y_{VH}(\alpha_0, t) = -x(\alpha_0, 2\pi - t)$ project $y_{VH}(\alpha_0, t)$ from the original frequency $\alpha_0$ to the target frequency $\alpha_1$, to find $\hat{y}(\alpha_1, t)$ $\hat{x}(\alpha_1, t) = \hat{y}(\alpha_1, 2\pi - t)$ Another method used by processor(s) 304 of converting the waveform to the optimized patterns may be to introduce a time shift ($\phi$) to the parametrized component. In the example of sine parametrization, the time shift may be introduced in the form of $y(\alpha, t) = \sin(\alpha(t-\phi))u(t)$.

Since, for horizontal flipping, this method uses a time shift in place of a reversal of the time sequence of the waveform, a restoration of the time sequence after projection is no longer necessary. That is, regardless of whether the converted waveform (y) has undergone horizontal flipping, projection of the original waveform ($\hat{x}$) will be the same as the projection of the converted waveform ($\hat{y}$): $\hat{x}(\alpha_1, t) = \hat{y}(\alpha_1, t)$.

Given the original waveform x over $t \in [0, 2\pi]$ and its zero-crossing ratio ($\delta$), the method of using a time shift may be performed as follows:

No flipping, for original waveform of {R, Rs, RS} patterns $\alpha_0 = 1/(2\delta)$ $y_0(\alpha_0, t) = x(\alpha_0, t) = \sin(\alpha_0(t-0))u(t)$ project $y_0(\alpha_0, t)$ from the original frequency $\alpha_0$ to the target frequency $\alpha_1$, to find $\hat{y}(\alpha_1, t)$ $\hat{x}(\alpha_1, t) = \hat{y}(\alpha_1, t)$ Flipping the vertical axis, for original waveform of {Q, Qr, QR} patterns $\alpha_0 = 1/(2\delta)$ $y_V(\alpha_0, t) = -\sin(\alpha t) u(t) = \sin(\alpha_0(t-\pi/\alpha_0))u(t)$ project $y_V(\alpha_0, t)$ from the original frequency $\alpha_0$ to the target frequency $\alpha_1$, to find $\hat{y}(\alpha_1, t)$ $\hat{x}(\alpha_1, t) = \hat{y}(\alpha_1, t)$ Flipping the horizontal axis, for original waveform of {qR} pattern $\alpha_0 = 1/(2(1-\delta))$ $y_H(\alpha_0, t) = \sin(\alpha(2\pi-t))u(t) = \sin(\alpha(t-(\pi/\alpha+2\pi)))u(t)$ project $y_H(\alpha_0, t)$ from the original frequency $\alpha_0$ to the target frequency $\alpha_1$, to find $\hat{y}(\alpha_1, t)$ $\hat{x}(\alpha_1, t) = \hat{y}(\alpha_1, t)$ Flipping both vertical and horizontal axes, for original waveform of {rS} pattern $\alpha_0 = 1/(2-\delta)$ $y_H(\alpha_0, t) = \sin(\alpha(2-t))u(t) = \sin(\alpha(t-2\pi))u(t)$ project $y_{VH}(\alpha_0, t)$ from the original frequency $\alpha_0$ to the target frequency $\alpha_1$, to find $\hat{y}(\alpha_1, t)$ $\hat{x}(\alpha_1, t) = \hat{y}(\alpha_1, t)$ Example 1—Example of Changing a First View to a Second View of a Waveform (Waveform Projection)

As an example, for changing a first view of a time series waveform to a second view (e.g., projecting an original waveform into a target or final waveform), processor(s) 304 (FIG. 3) may use the following combination of methods. The method of representing the parametrized component using a sinusoid function as the parametrized component described above may be applied. The method of parametrizing with a sinusoid function using a sine function as the parametrized component of $x(\alpha_0, t) = \sin(\alpha_0 t)u(t)$ described above may be applied. The time to first zero-crossing of the waveform may be determined as a proportion of the time span of the waveform to be projected ($\delta$), and the method of estimating the parameter of $\alpha_0$ described above may be applied by using the first zero-crossing after the start of the waveform as the half-period interval: $\hat{\alpha}_0 = \frac{1}{2}\delta$.

If $x(\alpha_0, t)$ is not of {R, Rs, RS} patterns, or if $x(\alpha_0, t)$ does not start with a dominant upright wave, then the method of extending projection described above may be applied by converting the waveform to {R, Rs, RS} patterns, using the method of converting the waveform of introducing a phase shift to the parametrized component of the waveform described above.

The method of mitigating inexact parameter estimates may be applied by searching through a range of trial frequencies $\alpha \in [\alpha_0 - \varepsilon, \alpha_0 - \varepsilon]$. For each trial frequency $\alpha$: the method of mitigation of singularities described above may be applied by identifying near-singularity points, using the method of identifying near-singularity status including: if $|\sin(\alpha t)| \geq \theta$ then the segment is not considered near-singularity; and determining the projected waveform using the method of replacing the parametrized component described above by sine-division: $\hat{x}(\alpha_1, t)=x(\alpha_0, t) \sin(\alpha_1 t)/\sin(\alpha t)$, such that if $|\sin(\alpha t)|<\theta$ then the segment is considered near-singularity. The segment may be set aside to be determined later using the method of alternative computation at near-singularity segments of cubic spline interpolation of the segments not considered near-singularity, as described above. A measure of discontinuity may be generated for this trial $\alpha$ using the method of computing a measurement of discontinuity of finding the maximum third difference throughout the entire waveform, for example. The discontinuity measurement of this trial $\alpha$ may be compared with all existing discontinuity measurements of all other trial $\alpha$'s. The $\alpha$ with the lowest discontinuity measurement may be $\alpha_0$, and the projected waveform may be the $\hat{x}(\alpha_1, t)$ associated with $\alpha_0$.

Figures 11, 11A, 11B, 11C:
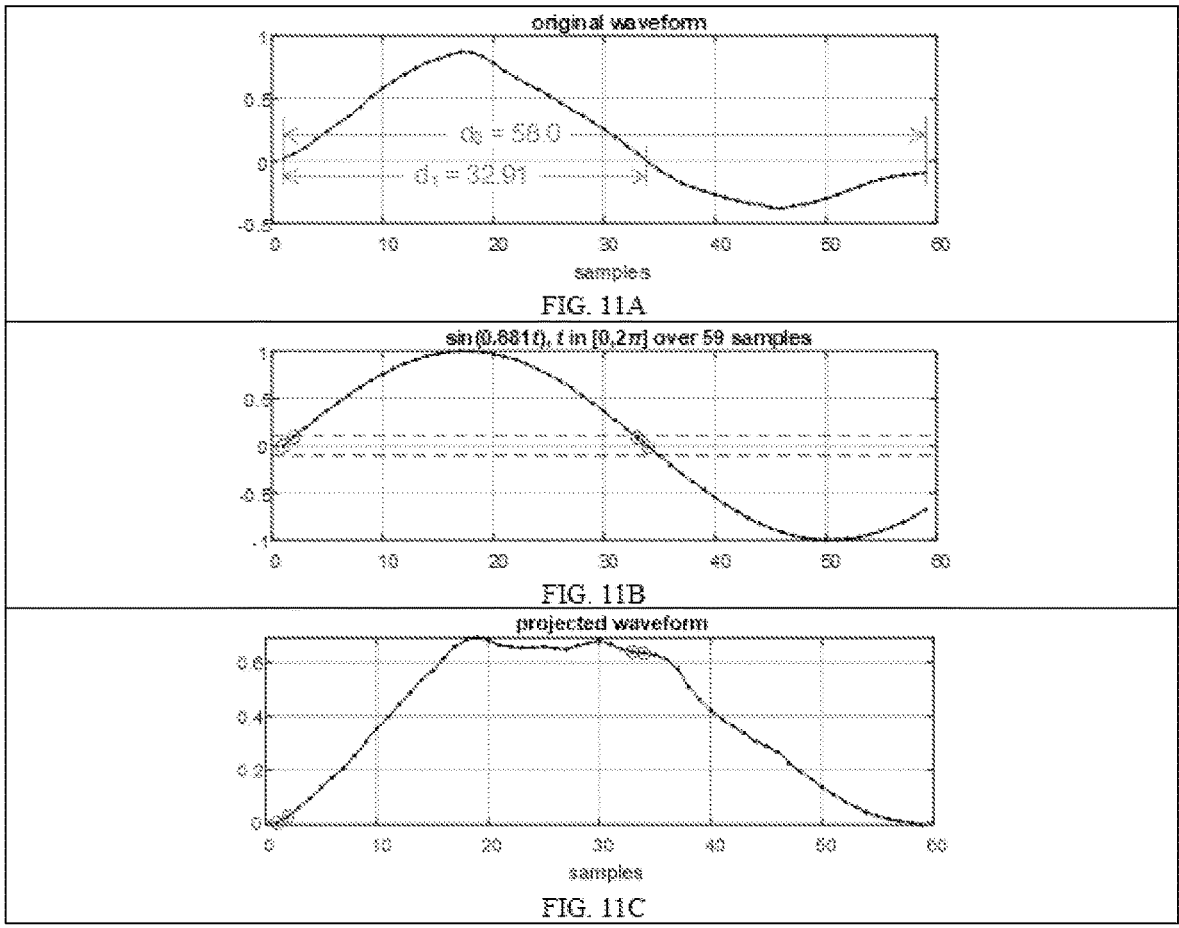
FIG. 11 illustrates changing a first view of a time series waveform to a second view.
FIG. 11A shows an example of an original (first view of a) ECG QRS complex time series waveform of an Rs-pattern.
FIG. 11B shows the corresponding sine wave with a sine frequency computed from the original ECG QRS waveform shown in FIG. 11A.
FIG. 11C shows the ECG QRS complex in FIG. 11A projected to an R-pattern waveform.

FIG. 11 illustrates an example of changing a first view of a time series waveform to a second view. FIG. 11A shows an example of an original (first view of a) ECG QRS complex time series waveform of an Rs-pattern. FIG. 11B shows the corresponding sine wave with a sine frequency computed from the original ECG QRS waveform shown in FIG. 11A. FIG. 11C shows the ECG QRS complex in FIG. 11A projected to an R-pattern waveform. For example, for the QRS of the ECG time series waveform in FIG. 11A, the original waveform is that of an Rs-pattern. The goal of changing the first view to a second view (e.g., projection) is to arrive at an R-pattern ($\alpha_1=0.5$) for this QRS time series waveform example. The span of this QRS waveform to map over $t \in [0, 2\pi]$ is over 59 samples ($d_0=58$). The first zero-crossing $d_1$ after the start of the waveform (at $t=0$) occurs between the 33rd and the 34th samples, as shown in FIG. 11B. Processor(s) 304 may be configured to find $\hat{a}_0$, using $\delta=d_1/d_0$. A more precise $d_1$ may be found by interpolating for the sub-sample zero-crossing between the 33rd and the 34th samples, which in this example is $d_1=32.91$. Hence, $\hat{\alpha}_0=\frac{1}{2}\delta=d_0/2d_1=0.881$. For some frequency $\alpha$ that is near $\hat{\alpha}_0$: processor(s) 304 may be configured to determine $$\hat{x}(0.5, t) = \frac{\sin(0.5t)}{\sin(\alpha t)} x(\alpha_0, t)$$

when $\sin(\alpha t)$ is not near zero, or otherwise interpolate for $\hat{x}(\alpha_1, t)$ using the determined samples if $|\sin(\alpha t)|<0.1$; and search values a $\alpha \in [0.881-0.05, 0.881+0.05]$ for a frequency that produces the minimum $D_m$, which is $\alpha=0.878$. The first view of the ECG QRS waveform that has been changed (e.g., projected) to a second view comprising an R-pattern ($\alpha_1=0.5$) is shown in FIG. 11C.

Example 2—Applications in Electrocardiography

Center of the QRS

The center of a QRS complex may be located at the point of maximum ventricular depolarization from the cardiac axis view of an ECG time series waveform. The center of the QRS complex may be used in determining pulse transition times, the pre-ejection period (PEP), or other measurements that may be used in determining left ventricular end diastolic pressure (LVEDP) or in indicating heart failure. The center of the QRS complex may also be used in determining the QT interval or QT dispersion, either of which may be used in assessing risk of lethal arrhythmias or in determining plasma electrolyte imbalance, including metabolic disorders such as diabetes mellitus.

Figure 12:
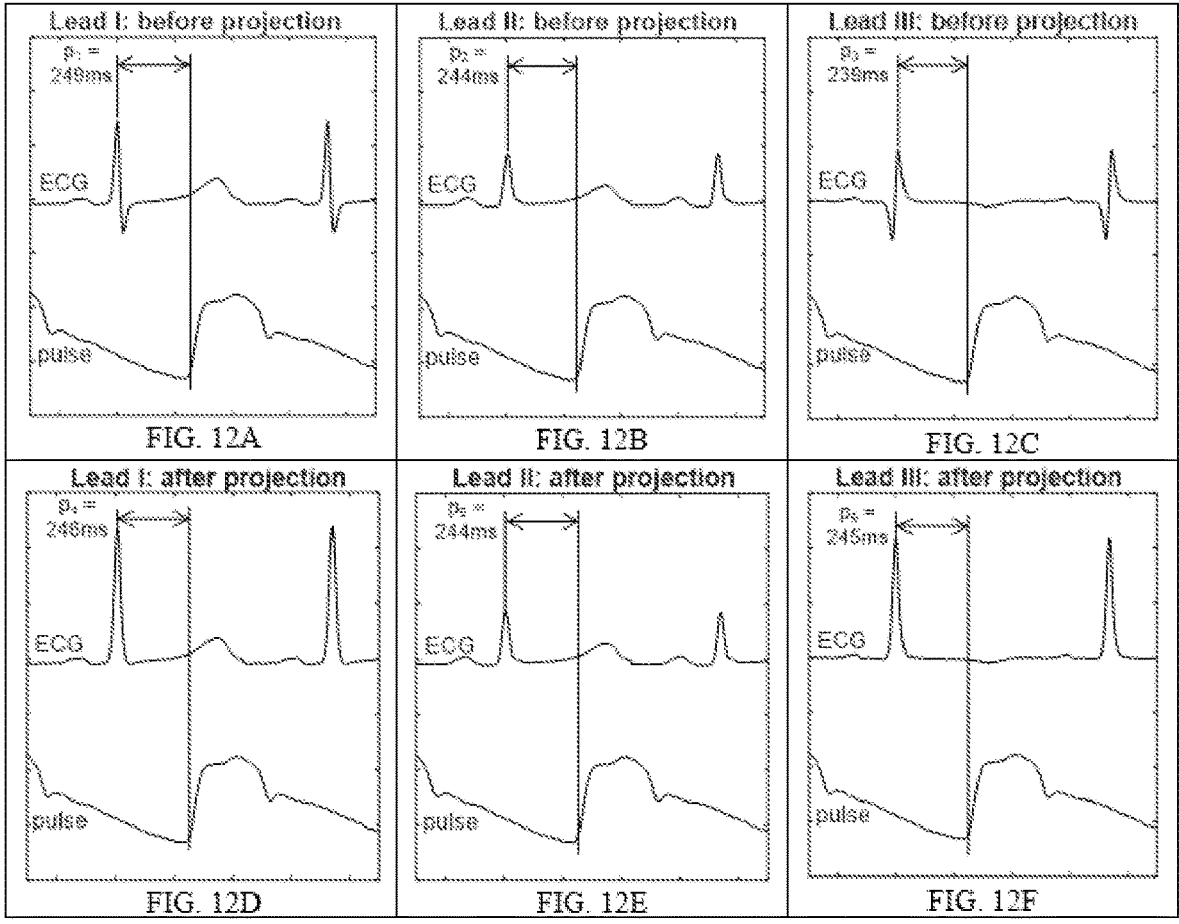
FIG. 12 shows measurements of pre-ejection period (PEP).

FIG. 12 shows measurements of PEP. FIG. 12 shows various measurements with various leads of an ECG. FIGS. 12A, 12B, and 12C respectively show the PEP measurements $p_1$, $p_2$, and $p_3$ measured from the QRS complexes of ECG leads I, II, and III of the same ECG to the start of the pulse, with a large variation in PEP, despite being measurements of the distance between the same QRS to the same pulse. After projecting the QRS complexes of these ECG leads I, II, and III to monophasic waveforms as shown respectively in FIGS. 12D, 12E, and 12F, the three PEP measurements $p_4$, $p_5$, and $p_6$ have significantly less variation. Using the operations described above, processor(s) 304 (FIG. 3) may be configured to find the center of the QRS by projecting (e.g., changing a first view to a second view of) the QRS complex time series waveform of the ECG to a waveform that is monophasic. For example, with sine parametrization of $x(\alpha, t)=\sin(\alpha t) u(t)$, $t \in [0, 2\pi]$, processor(s) 304 may be configured to project from the original parameter (frequency) of $\alpha_0$ to a parameter of $\alpha_1=0.5$. To mitigate potentially multiple peaks of pulsus bisferiens or signal artifacts, processor(s) 304 may fit a Gaussian function of approximate height and width as the projected waveform to the projected waveform. Processor(s) 304 may find the center of the QRS at the peak of the Gaussian function, for example.

Width of the QRS

The width of the QRS complex may be determined based on the width of ventricular depolarization from the cardiac axis view of the ECG time series waveform. An evaluation of a wide QRS may be indicative of intraventricular blocks, such as left bundle branch block (LBBB). An evaluation of a wide QRS may also be indicative of ventricular hypertrophy. In addition to being an indicator of heart disease, the presence of LBBB is also used in conventional criteria for determining ST elevation myocardial infarction (STEMI).

Figure 13:
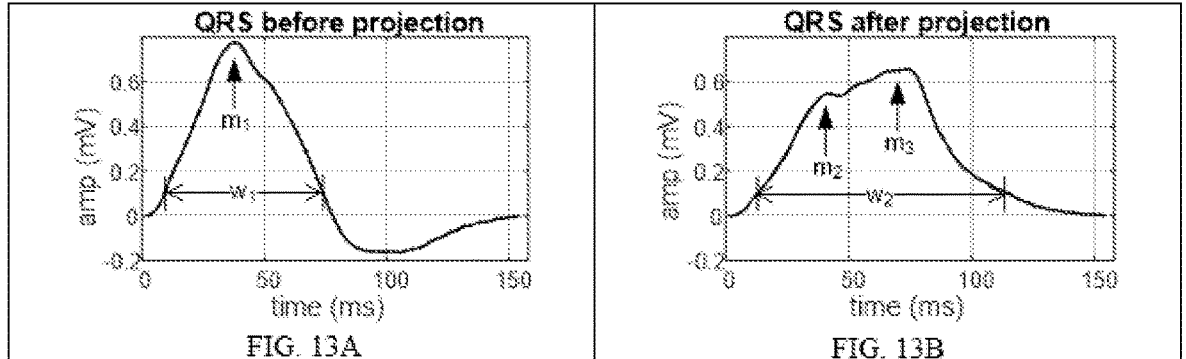
FIG. 13 shows another example of a waveform and its projection to reveal the presence of LBBB.

FIG. 13 shows another example of a waveform and its projection to reveal the presence of LBBB. FIG. 13A shows an example QRS with a width $w_1$ that is not sufficiently wide to be indicative of an LBBB. But when this QRS is projected onto its monophasic view as shown in FIG. 13B, its width is $w_2$, which is sufficiently wide to be indicative of an LBBB. Using the operations described above, processor(s) 304 may determine the width of the QRS by projecting (e.g., changing a first non-cardiac axis view of) the QRS of the ECG to a waveform that is monophasic (e.g., a second, cardiac axis view of the time series waveform). For example, with sine parametrization of $x(\alpha, t)=\sin(\alpha t) u(t)$, $t \in [0, 2\pi]$, projection from the original parameter (frequency value) of $\alpha_0$ to a parameter of $\alpha_1=0.5$ may be performed. Processor(s) 304 may determine the cross-sectional width of the monophasic projected waveform at 50% of the overall height of the projected QRS, for example. This cross-sectional width may be used to indicate wide QRS. A similar method may be applied to the width of the P-wave of the ECG to evaluate for a wide P-wave, which may be indicative of atrial enlargement.

Shape of the QRS

The shape of the QRS complex may be determined based on the shape of ventricular depolarization from the cardiac axis view of the ECG time series waveform. An evaluation of bimodal or multimodal peaks of a monophasic QRS complex may be indicative of intraventricular blocks, such as left bundle branch block (LBBB). An evaluation of the shape of the QRS may also be indicative of Brugada syndrome or chronic obstructive pulmonary disease (COPD). In addition to being an indicator of heart disease, the presence of LBBB is also used in conventional criteria for determining ST elevation myocardial infarction (STEMI). FIG. 13A shows an example QRS complex with a unimodal peak $m_1$ that is not indicative of an LBBB. But when this QRS complex is projected onto its monophasic view as shown in FIG. 13B, it is revealed to have bimodal peaks $m_2$ and $m_3$ that are indicative of an LBBB. Using the operations described above, processor(s) 304 may determine the width of the QRS by projecting (e.g., changing a first non-cardiac axis view of) the QRS of the ECG to a waveform that is monophasic (e.g., a second, cardiac axis view of the time series waveform). For example, with sine parametrization of $x(\alpha, t)=\sin(\alpha t)$ u(t), $t\in[0, 2\pi]$, projection from the original parameter (frequency value) of $\alpha_0$ to a parameter of $\alpha_1=0.5$ may be performed. Processor(s) 304 may determine the presence of bimodal or multimodal peaks based on the projected waveform. A similar method may be applied to flutter waves in the ECG to reveal the presence of atrial flutter.

ST Elevation/Depression

Indications of ST segment elevation or depression are located at the end of the QRS complex time-series waveform, and typically evaluated in millivolts. An evaluation of ST elevation/depression may be indicative of heart diseases and/or other disorders.

With multiple ECG leads, conventional evaluation of ST elevation/depression is done by finding the presence of ST elevation/depression above some voltage threshold in two or more contiguous ECG leads. Two conventional ECG leads may be defined as being contiguous if they are adjacent leads spaced some angle apart on a plane spanned by the two leads, for example 30° on the frontal plane. Two conventional ECG leads may also be defined as being contiguous if they belong to the same adjoining areas of tissue, such as leads I, aVL, V5, and V6, which all belong to the lateral wall of the left ventricle.

Figure 14:
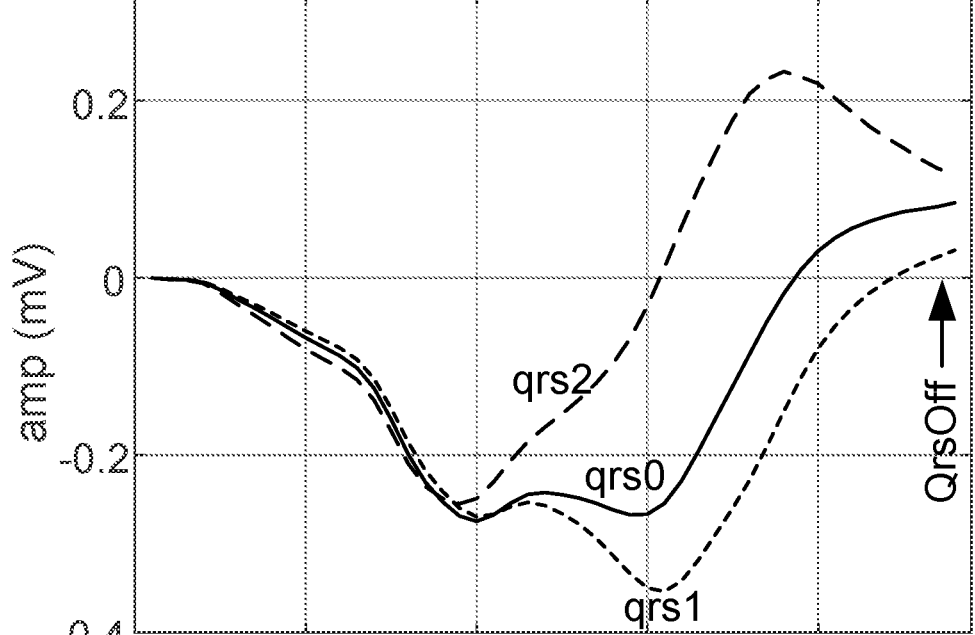
FIG. 14 shows a QRS complex projected onto $\pm 30°$ contiguous views.

FIG. 14 shows an example QRS complex qrs0 projected onto qrs1, a contiguous −30° view of qrs0, and projected onto qrs2, a contiguous +30° view of qrs0, each with a different value of ST at QRS offset (QrsOff) to provide for the evaluation of whether or not two contiguous leads have ST elevation above the voltage threshold. Processor(s) 304 may be configured to facilitate approximation of the ST elevation/depression of a contiguous lead relative to any ECG lead. The presence of ST elevation/depression may then be determined by evaluating a combination of actual leads and approximated contiguous leads for two or more contiguous leads having ST elevation/depression above some voltage threshold. Furthermore, ST elevation/depression as an indicator of ischemia, infarction, or reinfarction may be alternatively evaluated by their amplitudes relative to the overall amplitude of the QRS. Using the operations described above, evaluation of ST elevation/depression may be by processor(s) 304 by projecting the QRS time series waveform of the ECG to a waveform that is contiguous to the ECG. For example, with sine parametrization of $x(\alpha, t)=\sin(\alpha t)$ u(t), $t\in[0, 2\pi]$, projecting from the original parameter (frequency value) of $\alpha_0$ to a parameter of an $\alpha_1$ that is +30° from $\alpha_0$ or is −30° from $\alpha_0$ may be performed. The ST of the projected waveform may be determined. If the ST is elevated or depressed beyond a conventional threshold such as 1 mm (0.1 mV), then ST elevation/depression may be indicated for that threshold. The ST may also be determined as a fraction of the overall QRS amplitude of the projected waveform. If the fraction of ST over the amplitude of the projected QRS is above a certain threshold, then the presence of ST elevation/depression may be evaluated.

T-wave to QRS Amplitude Ratio

The T-wave to QRS (T-to-QRS) amplitude ratio is the amplitude of the T-wave as a proportion of the amplitude of the QRS complex. An evaluation of high T-to-QRS amplitude ratio or a high range of T-to-QRS amplitude ratios may be indicative of heart diseases and/or other disorders. In addition, T-to-QRS amplitude ratio is conventionally used in the case of hyper-acute T-waves to discern between aneurysm and infarction, to indicate unstable angina, or to determine plasma electrolyte imbalance, including metabolic disorders such as diabetes mellitus. With multiple ECG leads, conventional measurement of the T-to-QRS amplitude ratio is done by examining multiple leads on a plane, generally leads V2, V3, and V4. For each lead examined, the individual T-to-QRS amplitude ratio is computed by dividing the largest T-wave displacement by the largest QRS displacement. And the T-to-QRS amplitude ratio for the multi-lead ECG is the largest among these individual T-to-QRS amplitude ratios.

FIG. 15 illustrates measurement of T-wave to QRS amplitude ratio with associated projections. FIG. 15A shows an example of conventional measurement of the T-to-QRS amplitude ratio of a multi-lead ECG, by finding the individual T-to-QRS amplitude ratios of the largest T-wave deflection over the largest QRS deflection for its leads V2, V3, and V4, and finding the largest among these, which in this example is the individual ratio of V3. However, with a single or limited number of ECG leads, the range of the T-to-QRS ratio may be estimated and/or otherwise determined by finding the upper limit of its QRS amplitude as a "reference amplitude" by projecting the QRS of an ECG lead both to its monophasic view ($\alpha_1=0.5$), finding the lower limit of its QRS amplitude as a "reference amplitude" by projecting the QRS to its biphasic view ($\alpha_1=1.0$, finding the maximum T-wave amplitude as the "feature amplitude" by projecting the T-wave of an ECG lead to its monophasic view ($\alpha_1=0.5$), and finding the range of ratios by dividing the feature amplitude by these reference amplitudes. FIG. 15B shows an example of a single-lead ECG (lead V2 of the example in FIG. 15A) as well as this ECG with the QRS complex projected to a monophasic waveform and T-wave projected to a monophasic waveform, and their respective amplitudes ($\alpha_{QRS,M}$ and $\alpha_{T,M}$) to be used for estimating a lower limit of the T-to-QRS amplitude ratio ($R_{V2,M}=\alpha_{T,M}/\alpha_{QRS,M}$). FIG. 15C shows an example of a single-lead ECG (lead V2 of the example in FIG. 15A) as well as this ECG with the QRS complex projected to a biphasic waveform and T-wave projected to a monophasic waveform, and their respective amplitudes $\alpha_{QRS,B}$ and $\alpha_{T,M}$) to be used for estimating an upper limit of the T-to-QRS amplitude ratio ($R_{V2,B}=\alpha_{T,M}/\alpha_{QRS,B}$).

Using the operations described above, processor(s) 304 (FIG. 3) may be configured to find the range of amplitudes of the QRS complex on a plane by projecting (e.g., changing a first view to a second view of) the QRS complex time series waveform of the ECG to a waveform that is monophasic and a waveform that is biphasic, and finding their amplitudes as the "reference amplitudes." For example, with sine parametrization of $x(\alpha, t)=\sin(\alpha t)$ u(t), $t\in[0, 2\pi]$, processor(s) 304 may be configured to project from the original parameter (frequency) of $\alpha_0$ to parameters of $\alpha_1=0.5$ and $\alpha_1=1.0$. Processor(s) 304 may further be configured to find the largest amplitude of the T-wave on a plane by projecting (e.g., changing a first view to a second view of) the T-wave time series waveform of the ECG to another waveform that is monophasic, and finding its amplitude as the "feature amplitude." For example, with sine parametrization of $x(\alpha, t)=\sin(\alpha t)$ u(t), $t\in[0, 2\pi]$, processor(s) 304 may be configured to project from the original parameter (frequency) of $\alpha_0$ to a parameter of $\alpha_0=0.5$. To estimate the range of the T-to-QRS amplitude ratio, processor(s) 304 may further determine the ratios of the feature amplitude divided by the reference amplitudes.

QRS-T Angle

The QRS-T angle is the difference between the 3-dimensional (3D) vectors of the T-wave axis and the angle of the QRS complex axis. An evaluation of QRS-T angle may be indicative of heart diseases and/or other disorders. With a multi-lead ECG that spans 3D space, conventional measurement of the QRS-T is done in a representation of the multi-lead ECG in 3D space. In 3D space, the QRS complex and T-wave appear as loops (respectively QRS-loop and T-loop) that depart from the 3D origin (0,0,0) and return to the origin of the 3D origin. The conventional measurement of QRS-T angle is measured in 3D space by finding the vector from the origin to the QRS-loop maximum, finding the vector from the origin to the T-loop maximum, and finding the angular difference between these two vectors.

Figures 16, 16A, 16B:
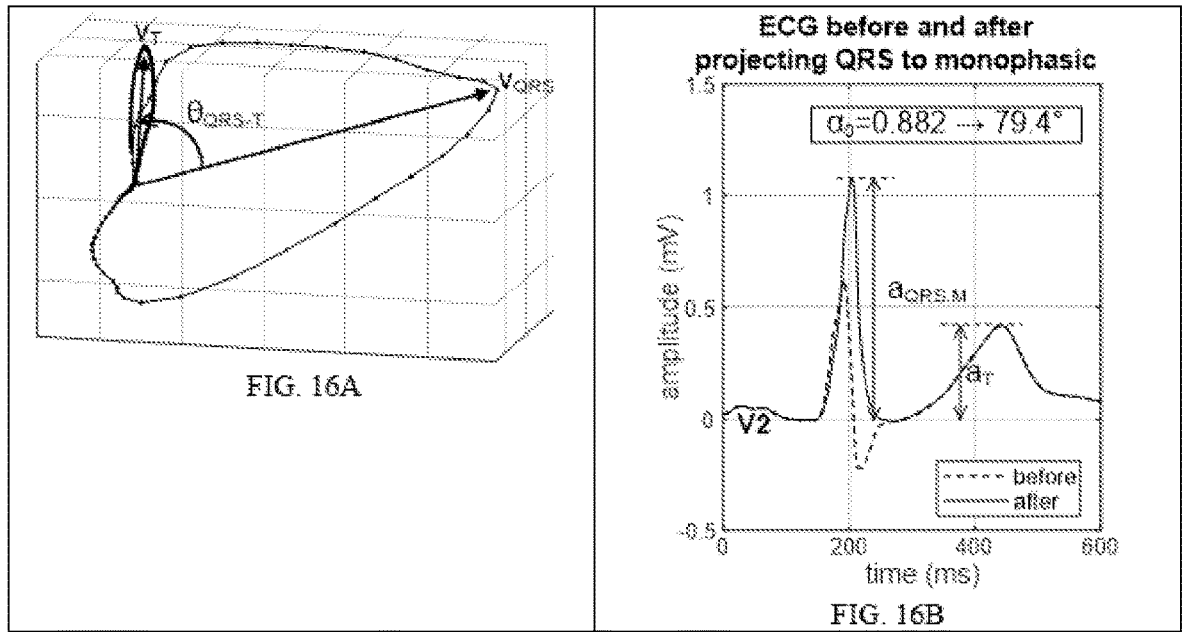
FIG. 16 illustrates differences between conventional measurement of QRS-T angle with an ECG in 3-dimensional space and determination of QRS-T angle with a single-lead ECG view of the same ECG.
FIG. 16A shows conventional measurement of QRS-T angle with an ECG in 3-dimensional space.
FIG. 16B shows determination of QRS-T angle with a single-lead ECG view of the same ECG shown in FIG. 16A.

FIG. 16 illustrates differences between conventional measurement of QRS-T angle with an ECG in 3-dimensional space and determination of QRS-T angle with a single-lead ECG view of the same ECG. FIG. 16A shows an example of conventional measurement of the QRS-T as the angular difference between the vector of the QRS-loop and the vector of the T-loop in 3D space. However, for an ECG with a single or limited number of leads that may not be sufficient to create an adequate representation in 3D space, the QRS-T angle may be estimated and/or otherwise determined by computing the angle of the QRS-loop vector relative to the viewpoint of the single-lead ECG as a "reference angle," estimating the angle of the T-loop vector relative to the viewpoint of the single-lead ECG as a "feature angle," and estimating the QRS-T angle by finding the difference between these two angles relative to the viewpoint of the single-lead ECG. A reference angle may be computed by finding the original parameter (frequency value) of the QRS complex, for example by finding the a, in with the sine parametrization of $x(\alpha, t)=\sin(\alpha t)\, u(t)$, $t \in [0, 2\pi]$, of the QRS complex. A feature angle representing the angle of the T-wave may be provided, or derived from the relative amplitude of the T-wave to the amplitude of a monophasic QRS complex and the shape of the T-wave. The relative amplitude of the T-wave to the amplitude of a monophasic QRS complex may be computed by dividing the amplitude of the T-wave by the amplitude of the QRS projected to a monophasic waveform.

FIG. 16B shows an example of computing the angle of the QRS by finding its original parameter ($\alpha_0$) and computing the amplitude of its monophasic waveform ($\alpha_{QRS,M}$). Using the operations described above, processor(s) 304 (FIG. 3) may be configured to find the angle of the QRS complex (reference angle). For example, with sine parametrization of $x(\alpha, t)=\sin(\alpha t)\, u(t)$, $t \in [0, 2\pi]$, of the QRS complex, processor(s) 304 may be configured to compute the original parameter (frequency) of $\alpha_0$ for the QRS complex, and also to create a projection from the original parameter (frequency) of $\alpha_0$ to a parameter of $\alpha_1=0.5$. Processor(s) 304 may be configured to compute a reference angle of the QRS complex based on $\alpha_0$. Processor(s) 304 may also be configured to derive a feature angle of the T-wave based on the amplitude of the T-wave relative to the amplitude of the projection of the QRS complex. Processor(s) 304 may be configured to compute the difference between the feature angle and the reference angle as an estimate of the QRS-T angle.

Applications in Electrocardiography Used in Conjunction

The applications in electrocardiography described above may also be used in conjunction with each other (in any combination). Some embodiments of the width of the QRS, the shape of the QRS, ST elevation or depression, T-wave to QRS amplitude ratio, and/or QRS-T angle used in conjunction may be indicative of heart diseases and/or other disorders. For example, the width and the shape of the QRS may be used in conjunction to evaluate the presence of left bundle branch block (LBBB). For example, such indication of presence of LBBB may be used in conjunction with the presence of ST elevation or depression to evaluate the presence of ST elevation myocardial infarction. For example, the presence of ST elevation or depression may be used in conjunction with T-wave to QRS amplitude ratio or QRS-T angle to evaluate the presence of infarction or aneurysm.

Returning to FIG. 3, one or more computing devices 306 may be and/or include a laptop computer, a tablet, a desktop computer, a smartphone, a gaming device, and/or other networked or non-networked computing devices, having a display, a user input device (e.g., buttons, keys, voice recognition, or a single or multi-touch touchscreen), memory (such as a tangible, machine-readable, non-transitory memory), a network interface, an energy source (e.g., a battery), and a processor such as a processor 304 (a term which, as used herein, includes one or more processors) coupled to each of these components. Memory such as electronic storage 338 of computing device 306 may store instructions that when executed by the associated processor provide an operating system and various applications, including a web browser or a native mobile application, for example. In addition, computing device 306 may include a user interface 336, which may include a monitor; a keyboard; a mouse; a touchscreen; etc. User interface 336 may be operative to provide a graphical user interface associated with system 300 that communicates with ECG system 302, and/or processor(s) 304, and facilitates user interaction with data from ECG system 302.

User interface 336 is configured to provide an interface between system 300 and users (e.g., a physician, etc.) through which users may provide information to and receive information from system 300. This enables data, results, and/or instructions, and any other communicable items, collectively referred to as "information," to be communicated between the users and one or more of ECG system 302, processor(s) 304, computing device 306, external resources 308, and/or other components. Examples of interface devices suitable for inclusion in user interface 336 include a keypad, buttons, switches, a keyboard, knobs, levers, a display screen, a touch screen, speakers, a microphone, an indicator light, an audible alarm, a printer, and/or other interface devices. In one embodiment, user interface 336 includes a plurality of separate interfaces (e.g., an interface that is part of ECG system 302, an interface in computing device 306, etc.). In one embodiment, user interface 336 includes at least one interface that is provided integrally with processor(s) 304. It is to be understood that many communication techniques, either hard-wired or wireless, between one or more components of system 300 are contemplated by the present disclosure. Other exemplary input devices and techniques adapted for use with system 300 as user interface 336 include, but are not limited to, an RS-232 port, RF link, an IR link, modem (telephone, cable or other). In short, any technique for communicating information with system 300 is contemplated by the present disclosure as user interface 336.

Electronic storage 338 comprises electronic storage media that electronically stores information. The electronic storage media of electronic storage 338 may include one or both of system storage that is provided integrally (i.e., substantially non-removable) with system 300 and/or removable storage that is removably connectable to system 300 via, for example, a port (e.g., a USB port, a firewire port, etc.) or a drive (e.g., a disk drive, etc.). Electronic storage 338 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 338 may store software algorithms, information determined by processor(s) 304, information received via user interface 336, and/or other information that enables system 300 to function properly. Electronic storage 338 may be (in whole or in part) a separate component within system 300, or electronic storage 338 may be provided (in whole or in part) integrally with one or more other components of system 300 (e.g., computing device 306, processor(s) 304, etc.).

External resources 308, in some embodiments, include sources of information such as databases, websites, etc.; external entities participating with system 300 (e.g., systems or networks associated with system 300), one or more servers outside of the system 300, a network (e.g., the internet), electronic storage, equipment related to Wi-Fi™ technology, equipment related to Bluetooth® technology, data entry devices, or other resources. In some implementations, some or all of the functionality attributed herein to external resources 308 may be provided by resources included in system 300. External resources 308 may be configured to communicate with one or more other components of system 300 via wired and/or wireless connections, via a network (e.g., a local area network and/or the internet), via cellular technology, via Wi-Fi technology, and/or via other resources.

Network 350 may include the internet, a Wi-Fi network, Bluetooth® technology, and/or other wireless technology. In some embodiments, ECG system 302, one or more processors 304, computing device 306, external resources 308, and/or other components of system 300 communicate via near field communication, Bluetooth, and/or radio frequency; via network 350 (e.g., a network such as a Wi-Fi network, a cellular network, and/or the internet); and/or by other communication methods.

In FIG. 3, ECG system 302, one or more processors 304, one or more computing devices 306, and/or other components of system 300 are shown as separate entities. This is not intended to be limiting. Some and/or all of the components of system 300 and/or other components may be grouped into one or more singular devices. For example, one or more processors 304 and computing device 306 may be included in ECG system 302. ECG system 302 and/or other components may be included in a wearable worn by a subject of an ECG. The wearable may be a watch, a band, one or more patches, a garment, a device, and/or other wearables. The wearable may be configured to be worn at or near the heart of the subject, for example. In some embodiments, the wearable may be and/or include a necklace, a chest strap, a shirt, a vest, and/or any other wearables configured such that system 300 can function as described herein.

The illustrated components of system 300 are depicted as discrete functional blocks, but embodiments are not limited to systems in which the functionality described herein is organized as illustrated by FIG. 3. The functionality provided by each of the components of system 300 may be provided by software or hardware modules that are differently organized than is presently depicted, for example such software or hardware may be intermingled, broken up, distributed (e.g. within a data center or geographically), or otherwise differently organized. Some or all of the functionality described herein may be provided by one or more processors of one or more computers executing code stored on a tangible, non-transitory, machine readable medium.

Figure 17:
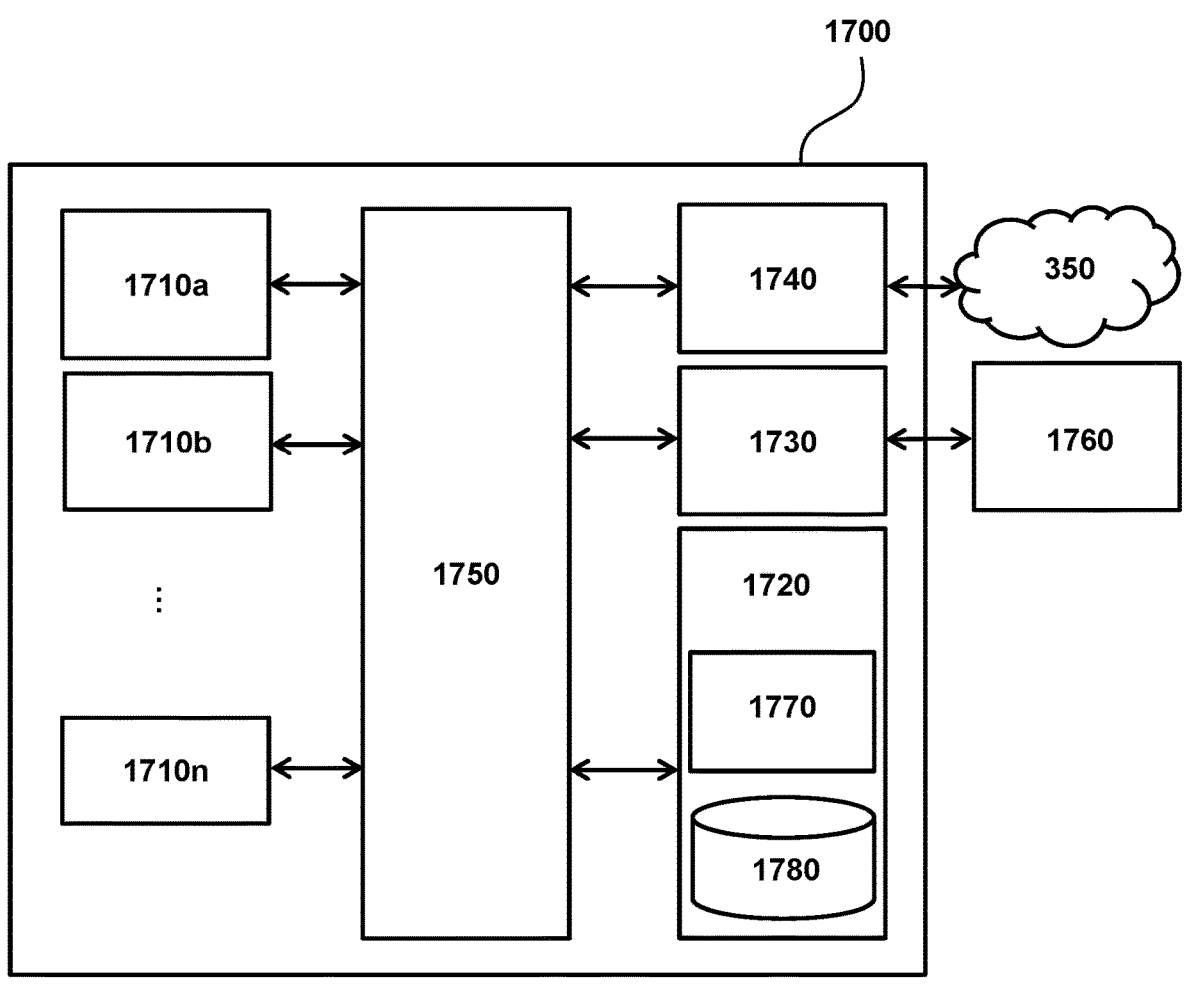
FIG. 17 is a diagram that illustrates an exemplary computing device in accordance with embodiments of the present system.

FIG. 17 is a diagram that illustrates an exemplary computing device 1700 (similar to and/or the same as computing device 306 described above) in accordance with embodiments of the present system. Various portions of systems and methods described herein, may include, or be executed on one or more computing devices the same as or similar to computing device 1700. For example, processor(s) 304 of system 300 (FIG. 3) may be and/or be included in one more computing devices the same as or similar to computing device 1700. Further, processes, modules, processor components, and/or other components of system 300 described herein may be executed by one or more processing systems similar to and/or the same as that of computing device 1700.

Computing device 1700 may include one or more processors (e.g., processors 1710a-1710n, which may be similar to and or the same as processor(s) 304) coupled to system memory 1720 (which may be similar to and/or the same as electronic storage 338), an input/output I/O device interface 1730, and a network interface 1740 via an input/output (I/O) interface 1750. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing device 1700. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 1720). Computing device 1700 may be a uni-processor system including one processor (e.g., processor 1710a), or a multi-processor system including any number of suitable processors (e.g., 1710a-1710n). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computing device 1700 may include a plurality of computing devices (e.g., distributed computer systems) to implement various processing functions.

I/O device interface 1730 may provide an interface for connection of one or more I/O devices 1760 to computer device 1700. I/O devices may include devices that receive input (e.g., from a user) or output information (e.g., to a user). I/O devices 1760 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 1760 may be connected to computing device 1700 through a wired or wireless connection. I/O devices 1760 may be connected to computing device 1700 from a remote location. I/O devices 1760 located on remote computer system, for example, may be connected to computing device 1700 via a network and network interface 1740.

Network interface 1740 may include a network adapter that provides for connection of computing device 1700 to a network (e.g., network 350 described above). Network interface may 1740 may facilitate data exchange between computing device 1700 and other devices connected to the network (e.g., network 350 shown in FIG. 3). Network interface 1740 may support wired or wireless communication. The network may include an electronic communication network, such as the Internet, a local area network (LAN), a wide area network (WAN), a cellular communications network, or the like.

System memory 1720 may be configured to store program instructions 1770 (e.g., machine readable instructions) or data 1780. Program instructions 1770 may be executable by a processor (e.g., one or more of processors 1710a-1710n) to implement one or more embodiments of the present techniques. Instructions 1770 may include modules and/or components of computer program instructions for implementing one or more techniques described herein with regard to various processing modules and/or components. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a standalone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 1720 may include a tangible program carrier having program instructions stored thereon. A tangible program carrier may include a non-transitory computer readable storage medium. A non-transitory computer readable storage medium may include a machine readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 1720 may include a non-transitory computer readable storage medium that may have program instructions stored thereon that are executable by a computer processor (e.g., one or more of processors 1710a-1710n) to cause the subject matter and the functional operations described herein. A memory (e.g., system memory 1720) may include a single memory device and/or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times, e.g., a copy may be created by writing program code to a first-in-first-out buffer in a network interface, where some of the instructions are pushed out of the buffer before other portions of the instructions are written to the buffer, with all of the instructions residing in memory on the buffer, just not all at the same time.

I/O interface 1750 may be configured to coordinate I/O traffic between processors 1710a-1710n, system memory 1720, network interface 1740, I/O devices 1760, and/or other peripheral devices. I/O interface 1750 may perform protocol, timing, or other data transformations to convert data signals from one component (e.g., system memory 1720) into a format suitable for use by another component (e.g., processors 1710a-1710n). I/O interface 1750 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computing device 1700 or multiple computing devices 1700 configured to host different portions or instances of embodiments. Multiple computing devices 1700 may provide for parallel or sequential processing/execution of one or more portions of the techniques described herein.

Those skilled in the art will appreciate that computing device 1700 is merely illustrative and is not intended to limit the scope of the techniques described herein. Computing device 1700 may include any combination of devices or software that may perform or otherwise provide for the performance of the techniques described herein. For example, computing device 1700 may include or be a combination of a cloud-computing system, a data center, a server rack, a server, a virtual server, a desktop computer, a laptop computer, a tablet computer, a server device, a client device, a mobile telephone, s smartphone, a personal digital assistant (PDA), a mobile audio or video player, a game console, a vehicle-mounted computer, or a Global Positioning System (GPS), or the like. Computing device 1700 may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computing device 1700 may be transmitted to computing device 1700 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present invention may be practiced with other computer system configurations.

Figure 18:
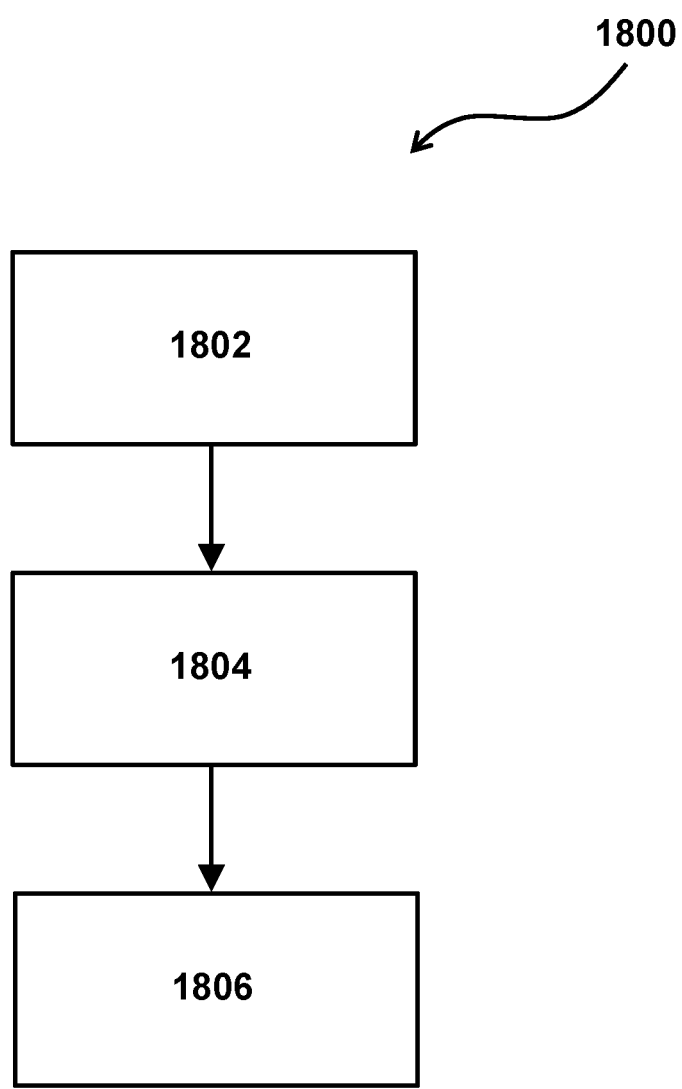
FIG. 18 is a flow chart that illustrates a method for changing a first view of a time series waveform to a second view.

FIG. 18 illustrates a method 1800 for changing a first view of a time series waveform to a second view. The first view of the time series waveform may be generated based on a single channel electrocardiogram (ECG) signal from an ECG system deployed in a patch, watch, or exercise equipment, for example. In some embodiments, the time series waveform comprises a monophasic or biphasic single channel QRS waveform associated with an ECG. In some embodiments, the time series waveform comprises a projection of a QRS loop. The second view of the time series waveform may be a projection along a planar QRS loop that is more favorable for morphologic interpretation compared to the first view.

The operations of method 1800 presented below are intended to be illustrative. In some embodiments, method 1800 may be accomplished with one or more additional operations not described, and/or without one or more of the operations discussed. Additionally, the order in which the operations of method 1800 are illustrated in FIG. 18 and described below is not intended to be limiting.

In some embodiments, some or all of method 1800 may be implemented in one or more processing devices (e.g., a digital processor, an analog processor, a digital circuit designed to process information, an analog circuit designed to process information, a state machine, and/or other mechanisms for electronically processing information). The one or more processing devices (e.g., processor(s) 304, processor 1710*a*, etc., described herein) may include one or more devices executing some or all of the operations of method 1800 in response to instructions stored electronically on an electronic storage medium (e.g., electronic storage 338, system memory 1720, etc.). The one or more processing devices may include one or more devices configured through hardware, firmware, and/or software to be specifically designed for execution of one or more of the operations of method 1800.

At an operation 1802, the first view of the time series waveform is separated into an unchanging intrinsic component and a changeable parameterized component. In some embodiments, the unchanging intrinsic component is upright and monophasic. In some embodiments, the parameterized component comprises a sinusoidal function and the first and second parameters comprise different frequencies of the sinusoidal function. The sinusoidal function may be a sine function or a cosine function, for example. In some embodiments, the parameterized component comprises a Taylor series expansion and the first and second parameters comprise different Taylor series. In some embodiments, operation 1802 is performed by or with a processor similar to and/or the same as processor(s) 304, processor 1710*a*, etc., (shown in FIG. 3 and FIG. 17, and described herein).

At an operation 1804, a first parameter of the changeable parameterized component associated with the first view is replaced with a second parameter associated with the second view. The first parameter of the changeable parameterized component associated with the first view may be determined based on a first zero crossing of the time series waveform, for example. In some embodiments, operation 1804 includes mitigating inexact parameter determinations by perturbation. Perturbation may comprise testing different parameter values to determine which parameter value provides a best changed time series waveform continuity (or least discontinuity). In some embodiments, discontinuity may be determined by determining slopes of the time series waveform preceding, during, and following singularity or near-singularity segments. In some embodiments, discontinuity may be determined by determining a largest third derivative throughout the second view of the time series waveform at each trial parameter value.

In some embodiments, replacing the first parameter with the second parameter comprises parameterized component division. Operation 1804 may include mitigating potential singularities or near-singularities caused by parameterized component division by identifying segments of the second view of the time series waveform that comprise the potential singularities or near-singularities, applying an alternative computation to change the first view to the second view at these potential singularity or near-singularity segments, and/or other operations. The potential singularities or near singularities may be identified based on a threshold on sines of frequencies of the first view of the time series waveform and/or by other operations.

In some embodiments, the alternative computation may be or include interpolation of the identified segments using the second view of the time series waveform at segments that are not near-zero, as determined by parametrized component replacement. In some embodiments, the alternative computation is performed using functional approximation, as the parametrized component with the second parameter approaches singularity. In some embodiments, operation 1804 is performed by or with a processor similar to and/or the same as processor(s) 304, processor 1710*a*, etc., (shown in FIG. 3 and FIG. 17, and described herein).

At an operation 1806, the first view is changed to the second view based on the unchanging intrinsic component and the changeable parameterized component with the second parameter. In some embodiments, operation 1806 is performed by or with a processor similar to and/or the same as processor(s) 304, processor 1710*a*, etc., (shown in FIG. 3 and FIG. 12, and described herein).

Method 1800 may be extended to, and/or the time series waveform may be converted to, other waveform patterns by flipping a time axis, flipping a waveform axis, changing the parameter, and/or introducing a shift to the parameterized component of the first view of the time series waveform. In some embodiments, method 1800 comprises performing the separating (operation 1802), replacing (operation 1804), and changing (operation 1806) to determine a center of a QRS complex, determine a width of the QRS complex, and/or determine ST elevation/depression and/or other cardiovascular diseases and/or conditions.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may provided by sending instructions to retrieve that information from a content delivery network.

As used herein, use of the word computing or estimated by generally be interchangeable with the word determining or similar phraseology.

Various embodiments of the present systems and methods are disclosed in the subsequent list of numbered clauses. In the following, further features, characteristics, and exemplary technical solutions of the present disclosure will be described in terms of clauses that may be optionally claimed in any combination:

1. A method for changing a first view of a time series waveform to a second view, the method comprising: separating the first view of the time series waveform into an unchanging intrinsic component and a changeable parameterized component; replacing a first parameter of the changeable parameterized component associated with the first view with a second parameter associated with the second view; and changing the first view to the second view based on the unchanging intrinsic component and the changeable parameterized component with the second parameter.

2. The method of clause 1, wherein the time series waveform comprises a monophasic or biphasic single channel QRS waveform associated with an electrocardiogram (ECG).

3. The method of any of the previous clauses, wherein the time series waveform comprises a projection of a QRS loop.

4. The method of any of the previous clauses, wherein the unchanging intrinsic component is upright and monophasic.

5. The method of any of the previous clauses, wherein the parameterized component comprises a sinusoidal function and the first and second parameters comprise different frequencies of the sinusoidal function.

6. The method of any of the previous clauses, wherein the sinusoidal function is a sine function or a cosine function.

7. The method of any of the previous clauses, wherein the parameterized component comprises a Taylor series expansion and the first and second parameters comprise different Taylor series.

8. The method of any of the previous clauses, wherein replacing the first parameter with the second parameter comprises parameterized component division.

9. The method of any of the previous clauses, further comprising mitigating potential singularities or near-singularities caused by parameterized component division by (a) identifying segments of the second view of the time series waveform that comprise the potential singularities or near-singularities, and (b) applying an alternative computation to change the first view to the second view at these potential singularity or near-singularity segments.

10. The method of any of the previous clauses, wherein the potential singularities or near singularities are identified based on a threshold on sines of frequencies of the first view of the time series waveform.

11. The method of any of the previous clauses, wherein the alternative computation comprises interpolation of the identified segments using the second view of the time series waveform at segments that are not near-zero, as determined by parametrized component replacement.

12. The method of any of the previous clauses, wherein the alternative computation is performed using functional approximation, as a parametrized component when the second parameter approaches singularity.

13. The method of any of the previous clauses, wherein the first parameter of the changeable parameterized component associated with the first view is determined based on a first zero crossing of the time series waveform.

14. The method of any of the previous clauses, further comprising mitigating inexact parameter determinations by perturbation, the perturbation comprising testing different parameter values to determine which parameter value provides a best changed time series waveform continuity (or least discontinuity).

15. The method of any of the previous clauses, further comprising determining discontinuity by determining slopes of the time series waveform preceding, during, and following singularity or near-singularity segments.

16. The method of any of the previous clauses, further comprising determining discontinuity by determining a largest third derivative throughout the second view of the time series waveform at each trial parameter value.

17. The method of any of the previous clauses, further comprising extending the method to, or converting the time series waveform to, other waveform patterns by flipping a time axis, flipping a waveform axis, changing the parameter, and/or introducing a shift to the parameterized component of the first view of the time series waveform.

18. The method of any of the previous clauses, wherein the first view of the time series waveform is generated based on a single channel electrocardiogram (ECG) signal from an ECG system deployed in a patch, watch, or exercise equipment.

19. The method of any of the previous clauses, wherein the second view of the time series waveform comprises a projection along a planar QRS loop that is more favorable for morphologic interpretation compared to the first view.

20. The method of any of the previous clauses, further comprising performing the separating, replacing, and changing to determine a center of a QRS complex, determine a width of the QRS complex, and/or determine ST elevation/depression or other cardiovascular diseases or conditions.

21. The method of any of the previous clauses, wherein changing the first view to the second view based on the unchanging intrinsic component and the changeable parameterized component with the second parameter comprises rotation and/or projection techniques.

22. The method of any of the previous clauses, wherein changing the first view to the second view based on the unchanging intrinsic component and the changeable parameterized component with the second parameter comprises finding a center of a QRS complex by projecting a QRS complex time series waveform of an ECG to a waveform that is monophasic, the method further comprising determining a left ventricular end diastolic pressure (LVEDP).

23. The method of any of the previous clauses, wherein changing the first view to the second view based on the unchanging intrinsic component and the changeable parameterized component with the second parameter comprises finding a width of a QRS complex and/or determining a shape of the QRS complex by projecting a QRS complex time series waveform of an ECG to a waveform that is monophasic, the method further comprising determining a left bundle branch block (LBBB).

24. The method of any of the previous clauses, wherein: the width of the QRS complex comprises a cross-section width of the monophasic projected waveform at 50% of an overall height of the projected waveform; and/or the shape of the QRS complex comprises bimodal peaks of the monophasic projected waveform.

25. The method of any of the previous clauses, wherein changing the first view to the second view based on the unchanging intrinsic component and the changeable parameterized component with the second parameter comprises determining ST elevation and/or depression by projecting a QRS complex time series waveform of an ECG to a waveform that is contiguous to an ECG waveform, the method further comprising determining myocardial infarction and/or ischemia based on the ST elevation and/or depression.

26. The method of any of the previous clauses, wherein changing the first view to the second view based on the unchanging intrinsic component and the changeable parameterized component with the second parameter comprises determining a T-to-QRS amplitude ratio that is an amplitude of a T-wave as a proportion of an amplitude of a QRS complex, the method further comprising determining myocardial infarction and/or ischemia based on the T-to-QRS amplitude ratio.

27. The method of any of the previous clauses, wherein changing the first view to the second view based on the unchanging intrinsic component and the changeable parameterized component with the second parameter comprises determining a QRS-T angle as the difference between 3-dimensional (3D) vectors of a T-wave axis and an angle of a QRS complex axis, the method further comprising determining myocardial infarction and/or ischemia based on the QRS-T angle.

28. The method of any of the previous clauses, wherein changing the first view to the second view based on the unchanging intrinsic component and the changeable parameterized component with the second parameter comprises determining a left ventricular end diastolic pressure (LVEDP), a left bundle branch block (LBBB), a width and or a shape of a QRS complex, an ST elevation and/or depression, a T-to-QRS amplitude ratio, a QRS-T angle, and/or a combination thereof, the method further comprising determining myocardial infarction and/or ischemia based on the LVEDP, the LBBB, the width and/or shape of the QRS complex, the ST elevation and/or depression, the T-to-QRS amplitude ratio, the QRS-T angle, and/or the combination thereof.

29. A non-transitory computer readable medium having instructions thereon, the instructions when executed by a computer causing the computer to perform operations comprising: separating a first view of a time series waveform into an unchanging intrinsic component and a changeable parameterized component; replacing a first parameter of the changeable parameterized component associated with the first view with a second parameter associated with a second view of the time series waveform; and changing the first view to the second view based on the unchanging intrinsic component and the changeable parameterized component with the second parameter.

30. The medium of clause 29, wherein the time series waveform comprises a monophasic or biphasic single channel QRS waveform associated with an electrocardiogram (ECG).

31. The medium of any of the previous clauses, wherein the time series waveform comprises a projection of a QRS loop.

32. The medium of any of the previous clauses, wherein the unchanging intrinsic component is upright and monophasic.

33. The medium of any of the previous clauses, wherein the parameterized component comprises a sinusoidal function and the first and second parameters comprise different frequencies of the sinusoidal function.

34. The medium of any of the previous clauses, wherein the sinusoidal function is a sine function or a cosine function.

35. The medium of any of the previous clauses, wherein the parameterized component comprises a Taylor series expansion and the first and second parameters comprise different Taylor series.

36. The medium of any of the previous clauses, wherein replacing the first parameter with the second parameter comprises parameterized component division.

37. The medium of any of the previous clauses, the operations further comprising mitigating potential singularities or near-singularities caused by parameterized component division by (a) identifying segments of the second view of the time series waveform that comprise the potential singularities or near-singularities, and (b) applying an alternative computation to change the first view to the second view at these potential singularity or near-singularity segments.

38. The medium of any of the previous clauses, wherein the potential singularities or near singularities are identified based on a threshold on sines of frequencies of the first view of the time series waveform.

39. The medium of any of the previous clauses, wherein the alternative computation comprises interpolation of the identified segments using the second view of the time series waveform at segments that are not near-zero, as determined by parametrized component replacement.

40. The medium of any of the previous clauses, wherein the alternative computation is performed using functional approximation, as a parametrized component when the second parameter approaches singularity.

41. The medium of any of the previous clauses, wherein the first parameter of the changeable parameterized component associated with the first view is determined based on a first zero crossing of the time series waveform.

42. The medium of any of the previous clauses, the operations further comprising mitigating inexact parameter determinations by perturbation, the perturbation comprising testing different parameter values to determine which parameter value provides a best changed time series waveform continuity (or least discontinuity).

43. The medium of any of the previous clauses, the operations further comprising determining discontinuity by determining slopes of the time series waveform preceding, during, and following singularity or near-singularity segments.

44. The medium of any of the previous clauses, the operations further comprising determining discontinuity by determining a largest third derivative throughout the second view of the time series waveform at each trial parameter value.

45. The medium of any of the previous clauses, the operations further comprising extending the method to, or converting the time series waveform to, other waveform patterns by flipping a time axis, flipping a waveform axis, changing the parameter, and/or introducing a shift to the parameterized component of the first view of the time series waveform.

46. The medium of any of the previous clauses, wherein the first view of the time series waveform is generated based on a single channel electrocardiogram (ECG) signal from an ECG system deployed in a patch, watch, or exercise equipment.

47. The medium of any of the previous clauses, wherein the second view of the time series waveform comprises a projection along a planar QRS loop that is more favorable for morphologic interpretation compared to the first view.

48. The medium of any of the previous clauses, the operations further comprising performing the separating, replacing, and changing to determine a center of a QRS complex, determine a width of the QRS complex, and/or determine ST elevation/depression or other cardiovascular diseases or conditions.

49. The medium of any of the previous clauses, wherein changing the first view to the second view based on the unchanging intrinsic component and the changeable parameterized component with the second parameter comprises rotation and/or projection techniques.

50. The medium of any of the previous clauses, wherein changing the first view to the second view based on the unchanging intrinsic component and the changeable parameterized component with the second parameter comprises finding a center of a QRS complex by projecting a QRS complex time series waveform of an ECG to a waveform that is monophasic, the operations further comprising determining a left ventricular end diastolic pressure (LVEDP) based on the center of the QRS complex.

51. The medium of any of the previous clauses, wherein changing the first view to the second view based on the unchanging intrinsic component and the changeable parameterized component with the second parameter comprises finding a width of a QRS complex and/or determining a shape of the QRS complex by projecting a QRS complex time series waveform of an ECG to a waveform that is monophasic, the operations further comprising determining a left bundle branch block (LBBB) based on the width and/or the shape of the QRS complex.

52. The medium of any of the previous clauses, wherein:
the width of the QRS complex comprises a cross-section width of the monophasic projected waveform at 50% of an overall height of the projected waveform; and/or
the shape of the QRS complex comprises bi-modal peaks of the monophasic projected waveform.

53. The medium of any of the previous clauses, wherein changing the first view to the second view based on the unchanging intrinsic component and the changeable parameterized component with the second parameter comprises determining ST elevation and/or depression by projecting a QRS complex time series waveform of an ECG to a waveform that is contiguous to an ECG waveform, the operations further comprising determining myocardial infarction and/or ischemia based on the ST elevation and/or depression.

54. The medium of any of the previous clauses, wherein changing the first view to the second view based on the unchanging intrinsic component and the changeable parameterized component with the second parameter comprises determining a T-to-QRS amplitude ratio that is an amplitude of a T-wave as a proportion of an amplitude of a QRS complex, the method further comprising determining myocardial infarction and/or ischemia based on the T-to-QRS amplitude ratio.

55. The medium of any of the previous clauses, wherein changing the first view to the second view based on the unchanging intrinsic component and the changeable parameterized component with the second parameter comprises determining a QRS-T angle as the difference between 3-dimensional (3D) vectors of a T-wave axis and an angle of a QRS complex axis, the method further comprising determining myocardial infarction and/or ischemia based on the QRS-T angle.

56. The medium of any of the previous clauses, wherein changing the first view to the second view based on the unchanging intrinsic component and the changeable parameterized component with the second parameter comprises determining a left ventricular end diastolic pressure (LVEDP), a left bundle branch block (LBBB), a width and or a shape of a QRS complex, an ST elevation and/or depression, a T-to-QRS amplitude ratio, a QRS-T angle, and/or a combination thereof, the method further comprising determining myocardial infarction and/or ischemia based on the LVEDP, the LBBB, the width and/or shape of the QRS complex, the ST elevation and/or depression, the T-to-QRS amplitude ratio, the QRS-T angle, and/or the combination thereof.

57. A system for changing a first view of a time series waveform to a second view, the system comprising: one or more processors configured to: separate the first view of the time series waveform into an unchanging intrinsic component and a changeable parameterized component; replace a first parameter of the changeable parameterized component associated with the first view with a second parameter associated with the second view; and change the first view to the second view based on the unchanging intrinsic component and the changeable parameterized component with the second parameter.

58. The system of clause 57, further comprising an electrocardiogram (ECG) system configured to generate one or more output signals conveying ECG information for a subject; wherein: the one or more processors are further configured to convert the one or more output signals into the first view of the time series waveform, the first view comprising a digital representation of the ECG information in the output signals; and the time series waveform comprises a monophasic or biphasic single channel QRS waveform associated with an ECG.

59. The system of any of the previous clauses, wherein the time series waveform comprises a projection of a QRS loop.

60. The system of any of the previous clauses, wherein the unchanging intrinsic component is upright and mono-phasic.

61. The system of any of the previous clauses, wherein the parameterized component comprises a sinusoidal function and the first and second parameters comprise different frequencies of the sinusoidal function.

62. The system of any of the previous clauses, wherein the sinusoidal function is a sine function or a cosine function.

63. The system of any of the previous clauses, wherein the parameterized component comprises a Taylor series expansion and the first and second parameters comprise different Taylor series.

64. The system of any of the previous clauses, wherein replacing the first parameter with the second parameter comprises parameterized component division.

65. The system of any of the previous clauses, wherein the one or more processors are further configured to miti-gate potential singularities or near-singularities caused by parameterized component division by (a) identify-ing segments of the second view of the time series waveform that comprise the potential singularities or near-singularities, and (b) applying an alternative com-putation to change the first view to the second view at these potential singularity or near-singularity segments.

66. The system of any of the previous clauses, wherein the potential singularities or near singularities are identi-fied based on a threshold on sines of frequencies of the first view of the time series waveform.

67. The system of any of the previous clauses, wherein the alternative computation comprises interpolation of the identified segments using the second view of the time series waveform at segments that are not near-zero, as determined by parametrized component replacement.

68. The system of any of the previous clauses, wherein the alternative computation is performed using functional approximation, as a parametrized component when the second parameter approaches singularity.

69. The system of any of the previous clauses, wherein the first parameter of the changeable parameterized com-ponent associated with the first view is determined based on a first zero crossing of the time series wave-form.

70. The system of any of the previous clauses, wherein the one or more processors are further configured to miti-gate inexact parameter determinations by perturbation, the perturbation comprising testing different parameter values to determine which parameter value provides a best changed time series waveform continuity (or least discontinuity).

71. The system of any of the previous clauses, wherein the one or more processors are further configured to deter-mine discontinuity by determining slopes of the time series waveform preceding, during, and following sin-gularity or near-singularity segments.

72. The system of any of the previous clauses, wherein the one or more processors are further configured to deter-mine discontinuity by determining a largest third derivative throughout the second view of the time series waveform at each trial parameter value.

73. The system of any of the previous clauses, wherein the one or more processors are further configured to flip a time axis, flip a waveform axis, change the parameter, and/or introduce a shift to the parameterized compo-nent of the first view of the time series waveform.

74. The system of any of the previous clauses, wherein the first view of the time series waveform is generated based on a single channel electrocardiogram (ECG) signal from an ECG system deployed in a patch, watch, or exercise equipment.

75. The system of any of the previous clauses, wherein the second view of the time series waveform comprises a projection along a planar QRS loop that is more favor-able for morphologic interpretation compared to the first view.

76. The system of any of the previous clauses, wherein the one or more processors are further configured to per-form the separating, replacing, and changing to deter-mine a center of a QRS complex, determine a width of the QRS complex, and/or determine ST elevation/depression or other cardiovascular diseases or condi-tions.

77. The system of any of the previous clauses, wherein the one or more processors are configured such that chang-ing the first view to the second view based on the unchanging intrinsic component and the changeable parameterized component with the second parameter comprises rotation and/or projection techniques.

78. The system of any of the previous clauses, wherein the one or more processors are configured such that chang-ing the first view to the second view based on the unchanging intrinsic component and the changeable parameterized component with the second parameter comprises finding a center of a QRS complex by projecting a QRS complex time series waveform of an ECG to a waveform that is monophasic, and the one or more processors are further configured to determine a left ventricular end diastolic pressure (LVEDP) based on the center of the QRS complex.

79. The system of any of the previous clauses, wherein the one or more processors are configured such that chang-ing the first view to the second view based on the unchanging intrinsic component and the changeable parameterized component with the second parameter comprises finding a width of a QRS complex and/or determining a shape of the QRS complex by projecting a QRS complex time series waveform of an ECG to a waveform that is monophasic, and the one or more processors are further configured to determine a left bundle branch block (LBBB) based on the width and/or the shape of the QRS complex.

80. The system of any of the previous clauses, wherein: the width of the QRS complex comprises a cross-section width of the monophasic projected waveform at 50% of an overall height of the projected waveform; and/or the shape of the QRS complex comprises bi-modal peaks of the monophasic projected waveform.

81. The system of any of the previous clauses, wherein the one or more processors are configured such that chang-ing the first view to the second view based on the unchanging intrinsic component and the changeable parameterized component with the second parameter comprises determining ST elevation and/or depression by projecting a QRS complex time series waveform of an ECG to a waveform that is contiguous to an ECG waveform, and the one or more processors are further configured to determine myocardial infarction and/or ischemia based on the ST elevation and/or depression.

82. The system of any of the previous clauses, wherein the one or more processors are configured such that changing the first view to the second view based on the unchanging intrinsic component and the changeable parameterized component with the second parameter comprises determining a T-to-QRS amplitude ratio that is an amplitude of a T-wave as a proportion of an amplitude of a QRS complex, the method further comprising determining myocardial infarction and/or ischemia based on the T-to-QRS amplitude ratio.

83. The system of any of the previous clauses, wherein the one or more processors are configured such that changing the first view to the second view based on the unchanging intrinsic component and the changeable parameterized component with the second parameter comprises determining a QRS-T angle as the difference between 3-dimensional (3D) vectors of a T-wave axis and an angle of a QRS complex axis, the method further comprising determining myocardial infarction and/or ischemia based on the QRS-T angle.

84. The system of any of the previous clauses, wherein the one or more processors are configured such that changing the first view to the second view based on the unchanging intrinsic component and the changeable parameterized component with the second parameter comprises determining a left ventricular end diastolic pressure (LVEDP), a left bundle branch block (LBBB), a width and or a shape of a QRS complex, an ST elevation and/or depression, a T-to-QRS amplitude ratio, a QRS-T angle, and/or a combination thereof, the method further comprising determining myocardial infarction and/or ischemia based on the LVEDP, the LBBB, the width and/or shape of the QRS complex, the ST elevation and/or depression, the T-to-QRS amplitude ratio, the QRS-T angle, and/or the combination thereof.

The reader should appreciate that the present application describes several inventions. Rather than separating those inventions into multiple isolated patent applications, applicants have grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to costs constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

What is claimed is:

1. A method for changing a first view of a time series waveform to a second view, the method comprising:

separating the first view of the time series waveform into an unchanging intrinsic component and a changeable parameterized component;

replacing a first parameter of the changeable parameterized component associated with the first view with a second parameter associated with the second view; and changing the first view to the second view based on the unchanging intrinsic component and the changeable parameterized component with the second parameter.

2. The method of claim 1, wherein the time series waveform comprises a monophasic or biphasic single channel QRS waveform associated with an electrocardiogram (ECG).

3. The method of claim 2, wherein the time series waveform comprises a projection of a QRS loop.

4. The method of claim 1, wherein the unchanging intrinsic component is upright and monophasic.

5. The method of claim 1, wherein the parameterized component comprises a sinusoidal function and the first and second parameters comprise different frequencies of the sinusoidal function.

6. The method of claim 5, wherein the sinusoidal function is a sine function or a cosine function.

7. The method of claim 1, wherein the parameterized component comprises a Taylor series expansion and the first and second parameters comprise different Taylor series.

8. The method of claim 1, wherein replacing the first parameter with the second parameter comprises parameterized component division.

9. The method of claim 1, further comprising mitigating potential singularities or near-singularities caused by parameterized component division by (a) identifying segments of the second view of the time series waveform that comprise the potential singularities or near-singularities, and (b) applying an alternative computation to change the first view to the second view at these potential singularity or near-singularity segments.

10. The method of claim 9, wherein the potential singularities or near singularities are identified based on a threshold on sines of frequencies of the first view of the time series waveform.

11. The method of claim 9, wherein the alternative computation comprises interpolation of the identified segments using the second view of the time series waveform at segments that are not near-zero, as determined by parametrized component replacement.

12. The method of claim 9, wherein the alternative computation is performed using functional approximation, as a parametrized component when the second parameter approaches singularity.

13. The method of claim 1, wherein the first parameter of the changeable parameterized component associated with the first view is determined based on a first zero crossing of the time series waveform.

14. The method of claim 1, further comprising mitigating inexact parameter determinations by perturbation, the perturbation comprising testing different parameter values to determine which parameter value provides a best changed time series waveform continuity (or least discontinuity).

15. The method of claim 14, further comprising determining discontinuity by determining slopes of the time series waveform preceding, during, and following singularity or near-singularity segments.

16. The method of claim 14, further comprising determining discontinuity by determining a largest third derivative throughout the second view of the time series waveform at each trial parameter value.

17. The method of claim 1, further comprising extending the method to, or converting the time series waveform to, other waveform patterns by flipping a time axis, flipping a waveform axis, changing the parameter, and/or introducing a shift to the parameterized component of the first view of the time series waveform.

18. The method of claim 1, wherein the first view of the time series waveform is generated based on a single channel electrocardiogram (ECG) signal from an ECG system deployed in a patch, watch, or exercise equipment.

19. The method of claim 18, wherein the second view of the time series waveform comprises a projection along a planar QRS loop that is more favorable for morphologic interpretation compared to the first view.

20. The method of claim 19, further comprising performing the separating, replacing, and changing to determine a center of a QRS complex, determine a width of the QRS complex, and/or determine ST elevation/depression or other cardiovascular diseases or conditions.

21. The method of claim 1, wherein changing the first view to the second view based on the unchanging intrinsic component and the changeable parameterized component with the second parameter comprises rotation and/or projection techniques.

22. The method of claim 1, wherein changing the first view to the second view based on the unchanging intrinsic component and the changeable parameterized component with the second parameter comprises finding a center of a QRS complex by projecting a QRS complex time series waveform of an ECG to a waveform that is monophasic, the method further comprising determining a left ventricular end diastolic pressure (LVEDP).

23. The method of claim 1, wherein changing the first view to the second view based on the unchanging intrinsic component and the changeable parameterized component with the second parameter comprises finding a width of a QRS complex and/or determining a shape of the QRS complex by projecting a QRS complex time series waveform of an ECG to a waveform that is monophasic, the method further comprising determining a left bundle branch block (LBBB).

24. The method of claim 23, wherein:

the width of the QRS complex comprises a cross-section width of a monophasic projected waveform at 50% of an overall height of the projected waveform; and/or the shape of the QRS complex comprises bi-modal peaks of the monophasic projected waveform.

25. The method of claim 1, wherein changing the first view to the second view based on the unchanging intrinsic component and the changeable parameterized component with the second parameter comprises determining ST elevation and/or depression by projecting a QRS complex time series waveform of an ECG to a waveform that is contiguous to an ECG waveform, the method further comprising determining myocardial infarction and/or ischemia based on the ST elevation and/or depression.

26. The method of claim 1, wherein changing the first view to the second view based on the unchanging intrinsic component and the changeable parameterized component with the second parameter comprises determining a T-to-QRS amplitude ratio that is an amplitude of a T-wave as a proportion of an amplitude of a QRS complex, the method further comprising determining myocardial infarction and/or ischemia based on the T-to-QRS amplitude ratio.

27. The method of claim 1, wherein changing the first view to the second view based on the unchanging intrinsic component and the changeable parameterized component with the second parameter comprises determining a QRS-T angle as the difference between 3-dimensional (3D) vectors of a T-wave axis and an angle of a QRS complex axis, the method further comprising determining myocardial infarction and/or ischemia based on the QRS-T angle.

28. The method of claim 1, wherein changing the first view to the second view based on the unchanging intrinsic component and the changeable parameterized component with the second parameter comprises determining a left ventricular end diastolic pressure (LVEDP), a left bundle branch block (LBBB), a width and or a shape of a QRS complex, an ST elevation and/or depression, a T-to-QRS amplitude ratio, a QRS-T angle, and/or a combination thereof, the method further comprising determining myocardial infarction and/or ischemia based on the LVEDP, the LBBB, the width and/or shape of the QRS complex, the ST elevation and/or depression, the T-to-QRS amplitude ratio, the QRS-T angle, and/or the combination thereof.

29. A non-transitory computer readable medium having instructions thereon, the instructions when executed by a computer causing the computer to perform operations comprising:

separating a first view of a time series waveform into an unchanging intrinsic component and a changeable parameterized component;

replacing a first parameter of the changeable parameterized component associated with the first view with a second parameter associated with a second view of the time series waveform; and changing the first view to the second view based on the unchanging intrinsic component and the changeable parameterized component with the second parameter.

30. The medium of claim 29, wherein the time series waveform comprises a monophasic or biphasic single channel QRS waveform associated with an electrocardiogram (ECG).

31. The medium of claim 30, wherein the time series waveform comprises a projection of a QRS loop.

32. The medium of claim 29, wherein the unchanging intrinsic component is upright and monophasic.

33. The medium of claim 29, wherein the parameterized component comprises a sinusoidal function and the first and second parameters comprise different frequencies of the sinusoidal function.

34. The medium of claim 33, wherein the sinusoidal function is a sine function or a cosine function.

35. The medium of claim 29, wherein the parameterized component comprises a Taylor series expansion and the first and second parameters comprise different Taylor series.

36. The medium of claim 29, wherein replacing the first parameter with the second parameter comprises parameterized component division.

37. The medium of claim 29, the operations further comprising mitigating potential singularities or near-singularities caused by parameterized component division by (a) identifying segments of the second view of the time series waveform that comprise the potential singularities or near-singularities, and (b) applying an alternative computation to change the first view to the second view at these potential singularity or near-singularity segments.

38. The medium of claim 37, wherein the potential singularities or near singularities are identified based on a threshold on sines of frequencies of the first view of the time series waveform.

39. The medium of claim 37, wherein the alternative computation comprises interpolation of the identified segments using the second view of the time series waveform at segments that are not near-zero, as determined by parametrized component replacement.

40. The medium of claim 37, wherein the alternative computation is performed using functional approximation, as a parametrized component when the second parameter approaches singularity.

41. The medium of claim 29, wherein the first parameter of the changeable parameterized component associated with the first view is determined based on a first zero crossing of the time series waveform.

42. The medium of claim 29, the operations further comprising mitigating inexact parameter determinations by perturbation, the perturbation comprising testing different parameter values to determine which parameter value provides a best changed time series waveform continuity (or least discontinuity).

43. The medium of claim 42, the operations further comprising determining discontinuity by determining slopes of the time series waveform preceding, during, and following singularity or near-singularity segments.

44. The medium of claim 42, the operations further comprising determining discontinuity by determining a largest third derivative throughout the second view of the time series waveform at each trial parameter value.

45. The medium of claim 29, the operations further comprising extending the operations to, or converting the time series waveform to, other waveform patterns by flipping a time axis, flipping a waveform axis, changing the parameter, and/or introducing a shift to the parameterized component of the first view of the time series waveform.

46. The medium of claim 29, wherein the first view of the time series waveform is generated based on a single channel electrocardiogram (ECG) signal from an ECG system deployed in a patch, watch, or exercise equipment.

47. The medium of claim 46, wherein the second view of the time series waveform comprises a projection along a planar QRS loop that is more favorable for morphologic interpretation compared to the first view.

48. The medium of claim 47, the operations further comprising performing the separating, replacing, and changing to determine a center of a QRS complex, determine a width of the QRS complex, and/or determine ST elevation/depression or other cardiovascular diseases or conditions.

49. The medium of claim 29, wherein changing the first view to the second view based on the unchanging intrinsic component and the changeable parameterized component with the second parameter comprises rotation and/or projection techniques.

50. The medium of claim 29, wherein changing the first view to the second view based on the unchanging intrinsic component and the changeable parameterized component with the second parameter comprises finding a center of a QRS complex by projecting a QRS complex time series waveform of an ECG to a waveform that is monophasic, the operations further comprising determining a left ventricular end diastolic pressure (LVEDP) based on the center of the QRS complex.

51. The medium of claim 29, wherein changing the first view to the second view based on the unchanging intrinsic component and the changeable parameterized component with the second parameter comprises finding a width of a QRS complex and/or determining a shape of the QRS complex by projecting a QRS complex time series waveform of an ECG to a waveform that is monophasic, the operations further comprising determining a left bundle branch block (LBBB) based on the width and/or the shape of the QRS complex.

52. The medium of claim 51, wherein:
the width of the QRS complex comprises a cross-section width of the monophasic projected waveform at 50% of an overall height of the projected waveform; and/or
the shape of the QRS complex comprises bi-modal peaks of the monophasic projected waveform.

53. The medium of claim 29, wherein changing the first view to the second view based on the unchanging intrinsic component and the changeable parameterized component with the second parameter comprises determining ST elevation and/or depression by projecting a QRS complex time series waveform of an ECG to a waveform that is contiguous to an ECG waveform, the operations further comprising determining myocardial infarction and/or ischemia based on the ST elevation and/or depression.

54. The medium of claim 29, wherein changing the first view to the second view based on the unchanging intrinsic component and the changeable parameterized component with the second parameter comprises determining a T-to-QRS amplitude ratio that is an amplitude of a T-wave as a proportion of an amplitude of a QRS complex, the method further comprising determining myocardial infarction and/or ischemia based on the T-to-QRS amplitude ratio.

55. The medium of claim 29, wherein changing the first view to the second view based on the unchanging intrinsic component and the changeable parameterized component with the second parameter comprises determining a QRS-T angle as the difference between 3-dimensional (3D) vectors of a T-wave axis and an angle of a QRS complex axis, the method further comprising determining myocardial infarction and/or ischemia based on the QRS-T angle.

56. The medium of claim 29, wherein changing the first view to the second view based on the unchanging intrinsic component and the changeable parameterized component with the second parameter comprises determining a left ventricular end diastolic pressure (LVEDP), a left bundle branch block (LBBB), a width and or a shape of a QRS complex, an ST elevation and/or depression, a T-to-QRS amplitude ratio, a QRS-T angle, and/or a combination thereof, the method further comprising determining myocardial infarction and/or ischemia based on the LVEDP, the LBBB, the width and/or shape of the QRS complex, the ST elevation and/or depression, the T-to-QRS amplitude ratio, the QRS-T angle, and/or the combination thereof.

* * * * *